US007914998B2

(12) United States Patent
Tissenbaum et al.

(10) Patent No.: US 7,914,998 B2
(45) Date of Patent: Mar. 29, 2011

(54) **NEUROTRANSMITTER SIGNALING CAN REGULATE LIFE SPAN IN *C. ELEGANS***

(75) Inventors: Heidi A. Tissenbaum, Wayland, MA (US); Christian Grove, Worcester, MA (US); Nenad Svrzikapa, Somerville, MA (US); Seung Wook Oh, Westborough, MA (US); Melissa Grabowski, Worcester, MA (US); Yamei Wang, Worcester, MA (US)

(73) Assignee: University of Massachusetts, Boston, MA (US)

( * ) Notice: Subject to any disclaimer, the term of this patent is extended or adjusted under 35 U.S.C. 154(b) by 338 days.

(21) Appl. No.: 10/813,324

(22) Filed: Mar. 29, 2004

(65) Prior Publication Data

US 2005/0044579 A1    Feb. 24, 2005

Related U.S. Application Data

(60) Provisional application No. 60/459,079, filed on Mar. 27, 2003.

(51) Int. Cl.
*G01N 33/53* (2006.01)
(52) U.S. Cl. .......................... 435/7.1; 435/7.22; 435/7.21
(58) Field of Classification Search .................. None
See application file for complete search history.

(56) References Cited

U.S. PATENT DOCUMENTS 6,225,120 B1    5/2001   Ruvkun et al.

OTHER PUBLICATIONS

Lane et al., 2002. Microscopy Research and Technique 59:335-338.*
Tatar (2003) Science 299:1346-1351.*
Nelson 2003. Genes & Development 17:813-818.*
Bymaster 2003. European Journal of Neuroscience 17:1403-1410.*
Ruvkun US Patent Application Publication 2001/0029617.*
Gomeza 2001. Life Sciences 68:2457-2466.*
Fordyce et al. 1991. J. Gerontol. 46:B245-248.*
Pasricha 1994. Gut 35:1319-1321.*
Dunant 1990. J. Physiol. Paris 84:211-219.*
Richardson 1991. Molecular Pharmacology 40:908-914.*
Gusovsky et al., European J Pharmacol. 1991; 206: 309-14.*
Borodic et al., Expert Opin Investig Drugs. 2001; 10: 1531-44.*
Tatar and Yin, Experimental Gerontology; 2001: 36: 723-738.*
Gems & Riddle, Genetics, 2000; 154: 1597-1610.*
Katic and Kahn, CMLS, 2005; 62: 320-343.*
Holzenberger et al., Nature, 2003; 421: 182-187.*
Ailion, Michael et al, "Neurosecretory control of aging in *Caenorhabditis elegans*," *Proc. Natl. Acad. Sci. USA*, vol. 96:7394-7397 (1999).
Ann, Kyoungsook et al, "Novel $Ca^{2+}$-binding Protein (CAPS) Related to UNC-31 Required for $Ca^{2+}$-activated Exocytosis," *The Journal of Biological Chemistry*, vol. 272(32):19637-19640 (1997).
Apfeld, Javier et al, "Cell Nonautonomy of *C. elegans* daf-2 Function in the Regulation of Diapause of Life Span," *Cell*, vol. 95:199-210 (1998).
Aravamudan, Bharathi et al, "*Drosophila* Unc-13 is essential for synaptic transmission," *Nature Neuroscience*, vol. 2(11):965-971 (1999).
Augustin, Iris et al, "Munc13-1 is essential for fusion competence of glutamatergic synaptic vesicles," *Nature*, vol. 400:457-461 (1999).
Barsyte, Dalia et al, "Longevity and heavy metal resistance in *daf-2* and *age-1* long-lived mutants of *Caenorhabditis elegans*," *FASEB J.*, vol. 15:627-634 (2001).
Brose, Nils et al, "Regulation of transmitter release by Unc-13 and its homologues," *Current Opinion in Neurobiology*, vol. 10:303-311 (2000).
Clancy, David J. et al, "Extension of Life-Span by Loss of CHICO, a *Drosophila* Insulin Receptor Substrate Protein," *Science*, vol. 292(5514):104-106 (2001).
Cutrer, F. Michael et al, "Antiepileptic Drugs in Migraine, Cluster Headache, and Mood Disorders," *Headache, The Journal of Head and Face Pain*, vol. 41(Suppl. 1):S3-S10 (2001).
Friedman, David B. et al, "A Mutation in the age-1 Gene in *Caenorhabditis elegans* Lengthens Life and Reduces Hermaphrodite Fertility," *Genetics*, vol. 118:75-86 (1988).
Gems, David et al, "Genetic, Behavioral and Environmental Determinants of Male Longevity in *Caenorhabditis elegans*," *Genetics*, vol. 154:1597-1610 (2000).
Hekimi, Siegfried et al, "Genetics and the Specificity of the Aging Process," *Science*, vol. 299(5611);1351-1354 (2003).
Honda, Yoko et al, "The daf-2 gene network for longevity regulates oxidative stress resistance and Mn-superoxide dismutase gene expression in *Caenorhabditis elegans*," *FASEB J.*, vol. 13:1385-1393 (1999).
Kawasaki, Masato et al, "A *Caenorhabditis elegans* JNK signal transduction pathway regulates coordinated movement via type-D GABAergic motor neurons," *The EMBO Journal*, vol. 18(13):3604-3615 (1999).
Kittler, Josef T. et al, "Mechanisms of $GABA_A$ Receptor Assembly and Trafficking," *Molecular Neurobiology*, vol. 26:251-268 (2002).
Klass, Michael R., "A Method for the Isolation of Longevity Mutants in the Nematode *Caenorhabditis elegans* and Initial Results," *Mechanisms of Ageing and Development*, vol. 22:279-286 (1983).
Koga, Makoto et al, "A *Caenorhabditis elegans* MAP kinase kinase, MEK-1, is involved in stress responses," *The EMBO Journal*, vol. 19(19):5148-5156 (2000).
Lackner, Mark R. et al, "Facilitation of Synaptic Transmission by EGL-30 Gqα and EGL-8 PLCβ: DAG Binding to UNC-13 Is Required to Stimulate Acetylcholine Release," *Neuron*, vol. 24:335-346 (1999).
Lithgow, Gordon J. et al, "Thermotolerance and extended life-span conferred by single-gene mutations and induced by thermal stress," *Proc. Natl. Acad. Sci. USA*, vol. 92:7540-7544 (1995).

(Continued)

*Primary Examiner* — Bridget E Bunner
*Assistant Examiner* — Christina Borgeest
(74) *Attorney, Agent, or Firm* — Nelson Mullins Riley & Scarborough LLP; Debra J. Milasincic, Esq.; Cynthia L. Kanik

(57) ABSTRACT

The present invention features methods of identifying modulators of longevity. Also featured are organisms, cell systems and compositions for performing those methods. Further featured are therapeutic methods for the use of modulators identified according to said methodologies.

21 Claims, 20 Drawing Sheets

OTHER PUBLICATIONS

Miller, Kenneth G. et al, "RIC-8 (Synembryn): A Novel Conserved Protein that Is Required for Gqα Signaling in the *C. elegans* Nervous System," *Neuron*, Vol. 27:289-299 (2000).

Miller, Kenneth G. et al, "G$_o$α and Diacylglycerol Kinase Negatively Regulate the Gqα Pathway in *C. elegans*," *Neuron*, vol. 24:323-333 (1999).

Murakami, Shin et al, "A Genetic Pathway Conferring Life Extension and Resistance to UV Stress in *Caenorhabditis elegans*," *Genetics*, vol. 143:1207-1218 (1996).

Nurrish, Stephen et al, "Serotonin Inhibition of Synaptic Transmission: Gα$_o$ Decreases the Abundance of UNC-13 at Release Sites," *Neuron*, vol. 24:231-242 (1999).

Owens, David F. et al, "Is There More to GABA than Synaptic Inhibition?" *Nat. Rev. Neuroscience*, vol. 3:715-727 (2002).

Richmond, Janet E. et al, "UNC-13 is required for synaptic vesicle fusion in *C. elegans*," *Nature Neuroscience*, vol. 2(11):959-964 (1999).

Richmond, Janet E. et al, "The synaptic vesicle cycle: exocytosis and endocytosis in *Drosophila* and *C. elegans*," *Current Opinion in Neurobiology*, vol. 12:499-507 (2002).

Sassa, Toshihiro et al, "Regulation of the UNC-18-*Caenorhabditis elegans* Syntaxin Complex by UNC-13," *The Journal of Neuroscience*, vol. 19(12):4772-4777 (1999).

Sutton, R. Bryan et al, "Crystal structure of a SNARE complex involved in synaptic exocytosis at 2.4 A resolution," *Nature*, vol. 395:347-353 (1998).

Tatar, M. et al, "Slow aging during insect reproductive diapause: why butterflies, grasshoppers and flies are like worms," *Experimental Gerontology*, vol. 36:723-738 (2001).

Villanueva, Alberto et al, "*jkk-1* and *mek-1* regulate body movement coordination and response to heavy metals through *jnk-1* in *Caenorhabditis elegans*," *The EMBO Journal*, vol. 20(18):5114-5128 (2001).

Wolkow, Catherine A. et al, "Regulation of *C. elegans* Life-Span by Insulinlike Signaling in the Nervous System," *Science*, vol. 290(5489):147-150 (2000).

Zhang, Wei et al, "Munc-18 Associates with Syntaxin and Serves as a Negative Regulator of Exocytosis in the Pancreatic β-Cell," *The Journal of Biological Chemistry*, vol. 275(52):41521-41527 (2000).

International Search Report for Application No. PCT/US04/09882, dated Jan. 14, 2005.

* cited by examiner

N2: 13.8 ± 0.6 days
egl-8(n488): 25 ± 1.1 days

N2: 19.4 ± 0.4 days dgk-1(nu62): 18.2 ± 0.4 days dgk-1(sa748): 16.5 ± 0.5 days goa-1(n363): 16.8 ± 1.0 days goa-1(n1134): 18 ± 0.5 days goa-1(sa734): 13.2 ± 1.0 days N2: 14.8 ± 0.5 days
unc-13(e450): 36.8 ± 1.0 days N2: 12.5 ± 0.5 days
unc-18(e81): 30.3 ± 0.6 days
unc-18(e234): 40.6 ± 0.9 days N2: 17 ± 0.7 days
cha-1(p1152): 24.5 ± 0.6 days N2: 16.6 ± 0.7 days
unc-13(e450): 38.3 ± 0.6 days
unc-13(e1091): 19.1 ± 0.4 days
daf-2(e1370): 52 ± 1.6 days
unc-13(e450); daf-2(e1370): 50.8 ± 0.7 days
unc-13(e1091); daf-2(e1370): 51.8 ± 0.7 days N2: 16.3 ± 0.6 days
daf-16(mu86): 13.8 ± 0.3 days
unc-18(e234): 36.5 ± 1.6 days
daf-16(mu86); unc-18(e234): 13.2 ± 0.4 days N2: 17.4 ± 0.5 days
daf-16(mu86): 16.2 ± 0.3 days
unc-13(e450): 36.7 ± 0.8 days
daf-16(mu86);unc-13(e450): 23 ± 0.4 days N2: 17.4 ± 0.5 days
egl-30(ad805): 26.9 ± 0.5 days
egl-30(ad806): 21.2 ± 0.7 days N2: 17.4 ± 0.5 days
egl-8(n488): 24.2 ± 0.5 days
egl-8(md1971): 26.2 ± 0.7 days N2: 17.4 ± 0.5 days
daf-16(mu86): 16.2 ± 0.3 days
egl-30(ad806): 21.2 ± 0.7 days
daf-16(mu86);egl-30(ad806): 20.0 ± 0.4 days N2: 17.4 ± 0.5 days
daf-2(e1370): 45.5 ± 1.9 days
egl-30(n686): 19.9 ± 0.4 days
daf-2(e1370);egl- 0(n686): 40.7 ± 1.7 days N2: 17.4 ± 0.5 days
daf-2(e1370): 45.5 ± 1.9 days
egl-8(md1971): 26.2 ± 0.7 days
daf-2(e1370);egl-8(md1971): 53.5 ± 1.3 days

NEUROTRANSMITTER SIGNALING CAN REGULATE LIFE SPAN IN C. ELEGANS

RELATED APPLICATIONS

This patent application claims the benefit of U.S. Provisional Patent Application Ser. No. 60/459,079, entitled "Neurotransmitter Signaling Can Regulate Life Span in *C. Elegans*", filed Mar. 27, 2003. The entire contents of the above-referenced provisional patent application are incorporated herein by this reference.

BACKGROUND OF THE INVENTION

Longevity genes are of obvious interest and importance, both for their life-extension potential and the possibility of their contributing to the enhancement of the quality of life. However, very few of these genes have been identified and even less is understood about how these genes act to prevent aging and promote life extension. Accordingly, there exists the need to discover genes whose function is associated with life-extension. These genes and their products would be useful in the screening for anti-aging agents and would serve as key targets in various anti-aging therapies. Ultimately, such tools could help to alleviate cognitive and motor function deficits in the aged population and thereby prolong the independence of the elderly.

The roundworm *C. elegans* has proved a valuable invertebrate model system to study aging owing to its short, reproducible life span and its amenability to genetic and molecular analysis. In molecular genetics, extended life span is one of the best indicators that an intervention in an aging process has been made, and the isolation of long-lived variants in *C. elegans* has provided important insights into the mechanisms of aging in the central nervous system. As the entire *C. elegans* genome is sequenced, it is feasible to envisage in the near future a comprehensive identification of all the genes that affect aging in this organism.

In *C. elegans*, the main pathway regulating life span is an insulin-like signaling pathway (Apfeld J. & Kenyon C. (1998) Cell 95: 199-210). The daf-2 gene encodes an insulin/IGF-like receptor and is a key molecule that regulates longevity. Mutations in daf-2 or other known signaling molecules in this pathway result in extended life span. The lifespan extension caused by mutations in daf-2 could be rescued when the daf-2 pathway signaling was restored specifically to neurons (C. A. Wolkow et al., (2000) Science 290 (5489):147-150). While the detailed mechanism of insulin signaling and its function in regulating longevity is becoming understood, additional players that regulate longevity remain to be identified. Genetic mosaic analysis of DAF-2 showed that daf-2 (−) cells display a phenotype of daf-2 (+). This result indicates that DAF-2 functions non-autonomously in the regulation of life span and suggests that additional pathways may regulate aging upstream of DAF-2 and the insulin signaling pathway. Indeed, signals from the germ line, mitochondria and sensory neurons in the head of the worm have been shown to regulate life span (S. Hekimi and L. Guarente (2003) Science, 299 (5611):1351-1354). The identification of new signaling pathways involved in regulating longevity could provide critical new targets for insulin regulators in higher organisms and potential anti-aging and Diabetes II targets for drug intervention in humans.

SUMMARY OF THE INVENTION

The present invention is based on the instant inventors' recently discovered insights into how the nervous system controls the lifespan of *C. elegans* through the daf-2 insulin-like signaling pathway. In particular, the instant inventors have examined the lifespan of strains having a reduction of function mutation in individual genes of several different neurotransmitter signaling pathways, including the acetylcholine, serotonin, dopamine, glutamate and gamma-aminobutyric acid (GABA) pathways. The instant inventors further constructed and examined the lifespan of double mutants containing a reduction-of-function mutation in neurotransmitter signaling pathways in combination with a loss or reduction-of-function mutation in daf-2, daf-16 or age-1 of the insulin signaling pathway.

The instant inventors have discovered that mutations that cause defects in the acetylcholine signaling pathway extend lifespan, and that this lifespan extension is mainly dependent upon daf-16. In contrast, reduction of function mutants in the serotonin signaling pathway shorten lifespan. These findings are consistent with the competing nature of the acetylcholine and serotonin pathways to regulate release of acetylcholine at synapses. The examination of reduction of function mutations in genes of the GABA signaling pathway alone, and in combination with insulin signaling pathway genes (daf-2 or daf-16), revealed that GABA signaling also regulates life span through a mechanism dependent upon daf-16. These findings indicate that the acetylcholine, GABA, and serotonin neurotransmitter signaling pathways play important roles in the lifespan determination of *C. elegans*, and further indicate that several genes in those pathways act upstream of daf-2 to regulate lifespan.

Accordingly, the present invention features methods of identifying modulators of longevity. Also featured are organisms, cell systems and compositions for performing those methods. Further featured are therapeutic methods featuring the use of modulators identified according to said methodologies.

Figure 1:
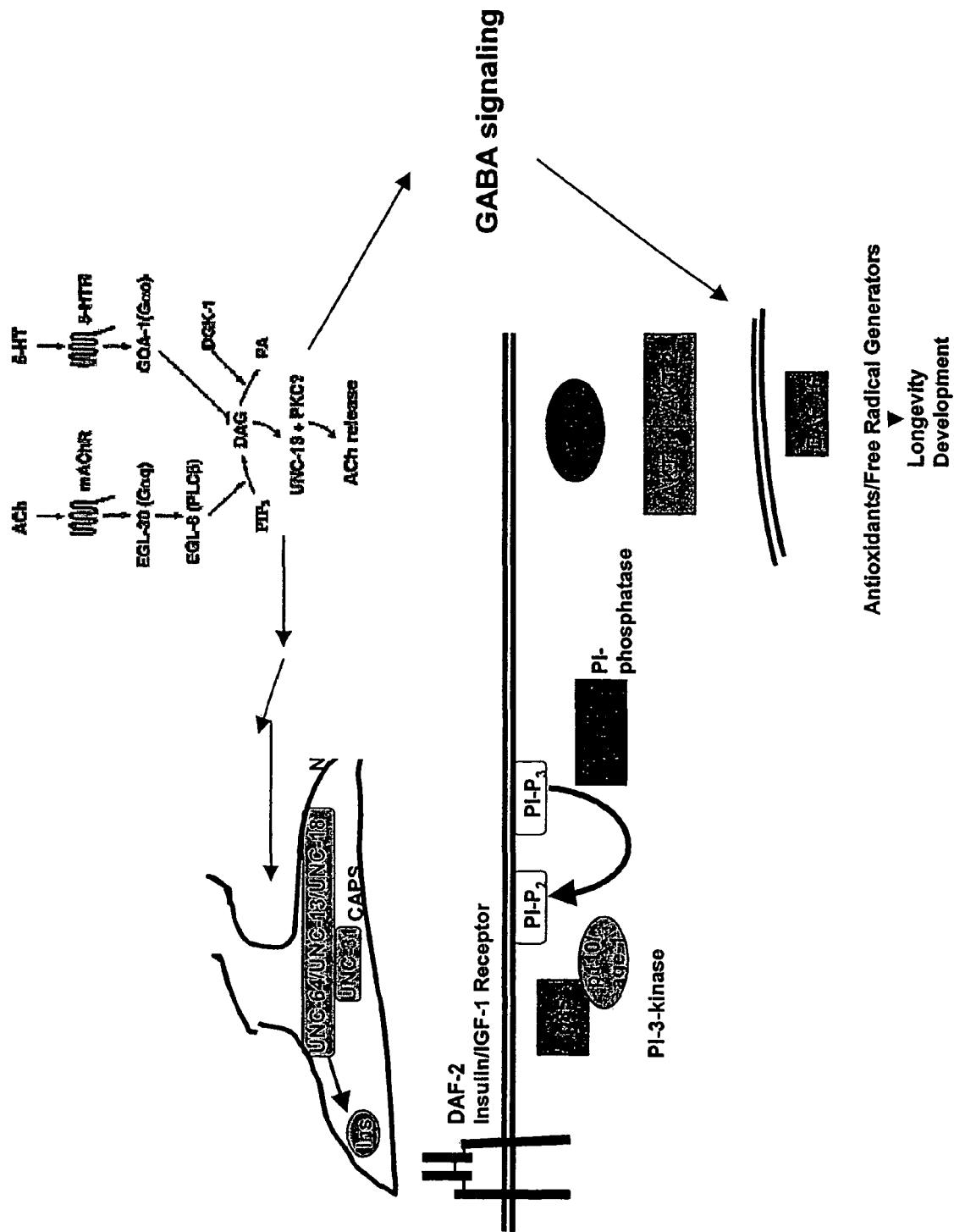
FIG. 1 is a schematic representation of neurotransmitter signaling pathways.

Other features and advantages of the invention will be apparent from the following detailed description and claims.

DETAILED DESCRIPTION OF THE INVENTION

The present invention is based, at least in part, on the discovery of a central role for neurotransmitter signaling pathways in controlling longevity. In particular, the invention is based on the discovery that reduction of function mutations in members of serotinergic, cholinergic and GABAergic neuromodulatory signaling pathways in *C. elegans* extend life span, and that regulation of life span by such neuromodulatory signaling pathways is at least partially dependent upon members of the insulin-like signaling pathway.

Accordingly, the invention features methods of identifying modulators of longevity in assays featuring organisms and/or cells having either a functional or deregulated neurotransmitter signaling pathway and, optionally, a functional or deregulated insulin-like signaling pathway. Also featured is an in vitro method of identifying an agent capable of enhancing longevity. Further featured are therapeutic methods featuring the use of neurotransmitter signaling pathway modulators in order to enhance longevity in a subject, for example, a human subject.

In one aspect, the invention features a method for identifying an agent capable of enhancing longevity, comprising contacting an organism having a deregulated neurotransmitter signaling pathway with a test agent, wherein a detectable phenotype is associated with said deregulated neurotransmitter signaling pathway, and assaying for the ability of the test agent to effect said phenotype, wherein the agent is identified based on its ability to alter said phenotype as compared to a suitable control.

In one embodiment of this aspect, said organism further has a deregulated insulin signaling pathway, wherein said detectable phenotype is associated with said deregulated neurotransmitter signaling pathway or said deregulated insulin signaling pathway.

In one embodiment, said neurotransmitter signaling pathway is a cholinergic pathway. In preferred embodiments, the organism has a deregulated neurotransmitter signaling pathway molecule selected from the group consisting of a muscarinic receptor, EGL-30 and EGL-8, or a mammalian orthologue of said signaling pathway molecule In one embodiment, said neurotransmitter signaling pathway is a serotinergic pathway. In preferred embodiments, the organism has a deregulated neurotransmitter signaling pathway molecule selected from the group consisting of a serotonin receptor, CAT-1, GOA-1 and DGK-1, or a mammalian orthologue of said signaling pathway molecule.

In another embodiment, the organism has a deregulated neurotransmitter signaling pathway molecule which is downstream of diacylglycerol (DAG) in a cholinergic or serotinergic pathway. In preferred embodiments, the organism has a deregulated neurotransmitter signaling pathway molecule selected from the group consisting of UNC-13, PKC, UNC-18, UNC-64, SNAP-25, synaptobrevin, UNC-31, or a mammalian orthologue of said signaling pathway molecule.

In yet other embodiments, said organism has a deregulated insulin signaling pathway molecule selected from the group consisting of DAF-2, AAP-1, IRS, AGE-1, PDK-1, AKT-1, AKT-2 and DAF-18, or a mammalian orthologue of said signaling pathway molecule.

In one embodiment, the phenotype is increased lifespan. In one embodiment, the phenotype is decreased lifespan. In a particular embodiment, the phenotype is constitutive dauer formation. In another embodiment, the phenotype is defective dauer formation.

In a second aspect, the instant invention features a method for identifying an agent capable of enhancing longevity, comprising contacting an organism with a test agent, said organism having a neurotransmitter signaling pathway, and assaying for the ability of the test agent to affect an indicator of said neurotransmitter signaling pathway, wherein the agent is identified based on its ability to alter said indicator as compared to a suitable control.

In a related aspect, the instant invention features a method for identifying an agent capable of enhancing longevity, comprising contacting an organism with a test agent, said organism having a neurotransmitter signaling pathway and an insulin signaling pathway, and assaying for the ability of the test agent to affect at least one indicator of neurotransmitter signaling or insulin signaling, wherein the agent is identified based on its ability to alter said indicator as compared to a suitable control.

In one embodiment, the indicator is a signaling pathway molecule or a reporter of said molecule.

In various embodiments, the agent is identified based on its ability to alter expression of said indicator, to alter an intracellular or extracellular level of said indicator, to alter an activity of said indicator, or to alter the cellular localization of said indicator.

In a preferred embodiment of the above aspects, the organism is a nematode, e.g., *C. elegans*. In one embodiment, the nematode is a parasitic nematode.

In a third aspect, the invention features a method for identifying an agent capable of enhancing longevity, comprising contacting a cell with a test agent, said cell having a neurotransmitter signaling pathway, and detecting an indicator of said neurotransmitter signaling pathway, wherein an agent is identified based on its ability to modulate the neurotransmitter signaling pathway in said cell.

In a related aspect, the invention features a method for identifying an agent capable of enhancing longevity, comprising contacting a cell with a test agent, said cell having a neurotransmitter signaling pathway and an insulin signaling pathway, and detecting an indicator of said neurotransmitter signaling pathway or insulin signaling pathway, wherein an agent is identified based on its ability to modulate the neurotransmitter signaling pathway or insulin signaling pathway in said cell.

In yet another related aspect, the invention features a method for identifying an agent capable of enhancing longevity, comprising contacting a cell population with a test agent, said population comprising a cell having a neurotransmitter signaling pathway and a cell having an insulin signaling pathway, and detecting an indicator of the neurotransmitter signaling pathway or insulin signaling pathway, wherein an agent is identified based on its ability to modulate the neurotransmitter signaling pathway or insulin signaling pathway.

In various embodiments of these aspects, the neurotransmitter signaling pathway is a serotinergic pathway, a cholinergic pathway, or a gamma-aminobutyric acid (GABA) signaling pathway.

In one embodiment, the agent is identified based on its ability to activate neurotransmitter signaling in said cell. In another embodiment, the agent is identified based on its ability to inhibit neurotransmitter signaling in said cell. In yet another embodiment, the agent is identified based on its ability to modulate neurotransmitter signaling and insulin signaling.

In one embodiment, the indicator is a signaling pathway molecule or a reporter of said molecule. In one embodiment, the agent is identified based on its ability to alter expression of said indicator.

In one embodiment, the agent is identified based on its ability to alter an intracellular or extracellular level of said indicator, to alter an activity of said indicator, or to alter the cellular localization of said indicator.

In one embodiment of these aspects of the invention, the cells are mammalian cells, e.g., human cells. In one embodiment, the cells are derived from a nematode.

In one embodiment of these aspects, the cell population comprises presynaptic cells and postsynaptic cells. In a preferred embodiment, the presynaptic cells are nerve cells. In another preferred embodiment, the postsynaptic cells are nerve cells. In still another preferred embodiment, the postsynaptic cells are muscle cells.

In a fourth aspect, the invention features a method for identifying an agent capable of enhancing longevity, comprising contacting an assay composition with a test compound, wherein said assay composition comprises a neurotransmitter signaling pathway molecule, and detecting activity or expression of said neurotransmitter signaling pathway molecule, wherein said agent is identified based on its ability to modulate activity or expression of said neurotransmitter signaling pathway molecule.

In one embodiment, the agent is identified based on its ability to inhibit activity or expression of said neurotransmitter signaling pathway molecule. In one embodiment, the agent is identified based on its ability to enhance activity or expression of said neurotransmitter signaling pathway molecule.

In a preferred embodiment of this aspect, the assay composition is a cell-free extract.

The invention further features novel agents identified according to the methods of any of the above aspects of the invention. Further featured are pharmaceutical compositions comprising the agents of the invention.

In a final aspect, the invention features a method of enhancing longevity in a subject, comprising administering to a subject in need of enhanced longevity a pharmacologically effective dose of an agent that modulates a neurotransmitter signaling pathway molecule, wherein modulation of said neurotransmitter signaling pathway molecule in said subject enhances longevity. In a related aspect, the method further comprises administering a pharmacologically effective dose of an agent that inhibits an insulin signaling pathway molecule.

In one embodiment, the agent modulates expression or activity of said neurotransmitter signaling pathway molecule.

In one embodiment, the subject is an aging or aged subject. In another aspect, the subject exhibits at least one symptom of premature aging. In yet another aspect, the subject has an aging-associated disorder.

So that the invention may be more readily understood, certain terms are first defined.

"Longevity" and "life-extension", used interchangeably herein, refer to any delay and/or stabilization of the aging process. Preferably, the longevity is due to an extension of the mature life phase, as opposed to an extension of the immature life phase (i.e., delay in maturity).

A "function" of a polynucleotide can be on any level, including DNA binding, transcription, translation, processing and/or secretion of expression product, interaction (such as binding) of expression product with another moiety, and regulation (whether repression or de-repression) of other genes. It is understood that a life-extension polynucleotide or polypeptide includes fragments, or regions, of a polynucleotide or polypeptide, as long as the requisite life-extension phenotype is observed.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

A "gerontogene" is a gene, the alteration of which slows aging, extends lifespan and/or enhances late-life health. See e.g., Rattan (1985) *Bioessays* 2:226-228. Such genes can also be termed "longevity assurance genes" or "longevity associated genes" (both abbreviated "LAGs"). See e.g., D'Mello et al., (1994) *J. Biol. Chem.* 269:15451-15459.

Figure 19:
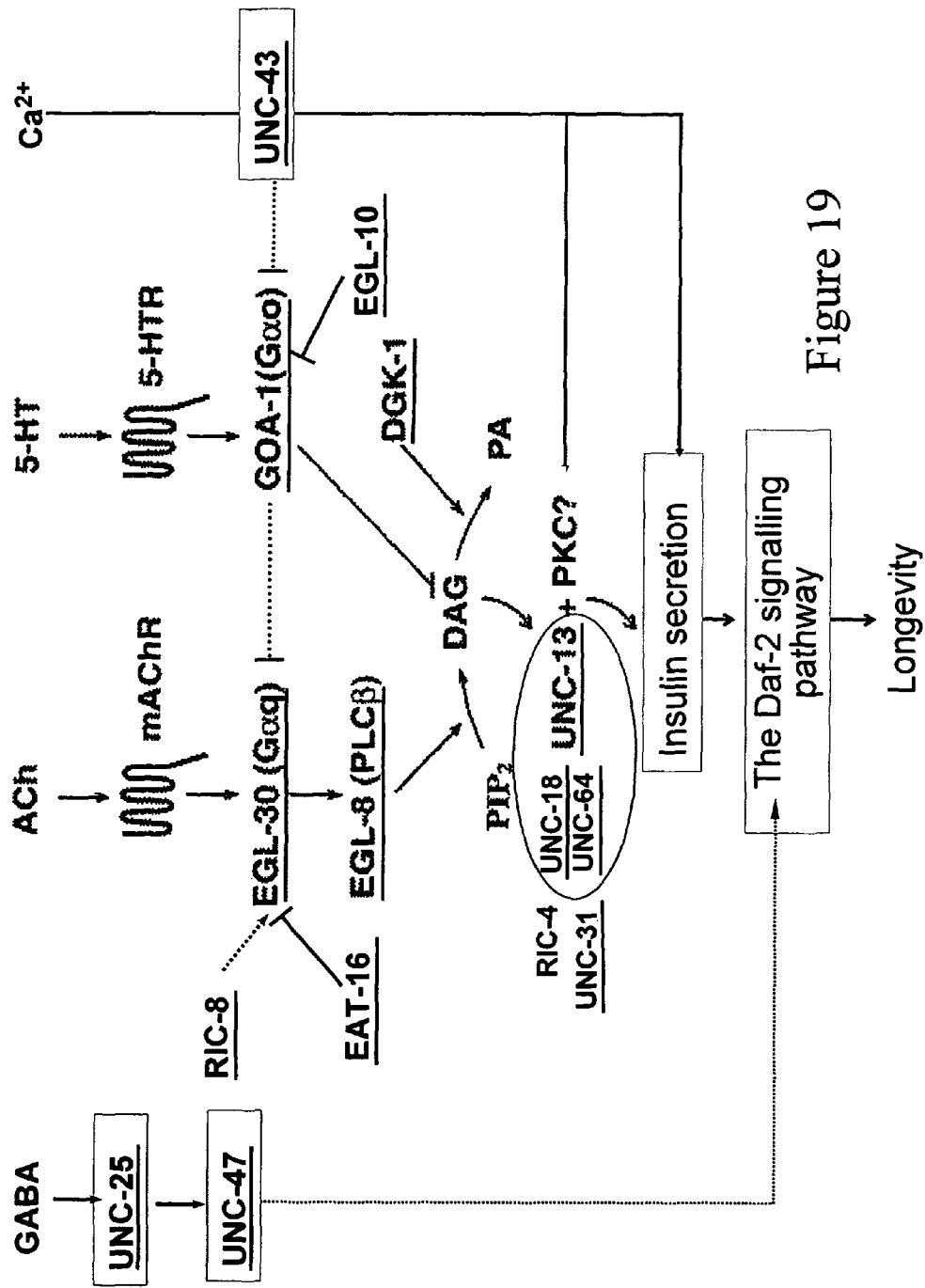
FIG. 19 is a schematic representation of neurosecretory control of aging in *C. elegans*.
Figure 20:
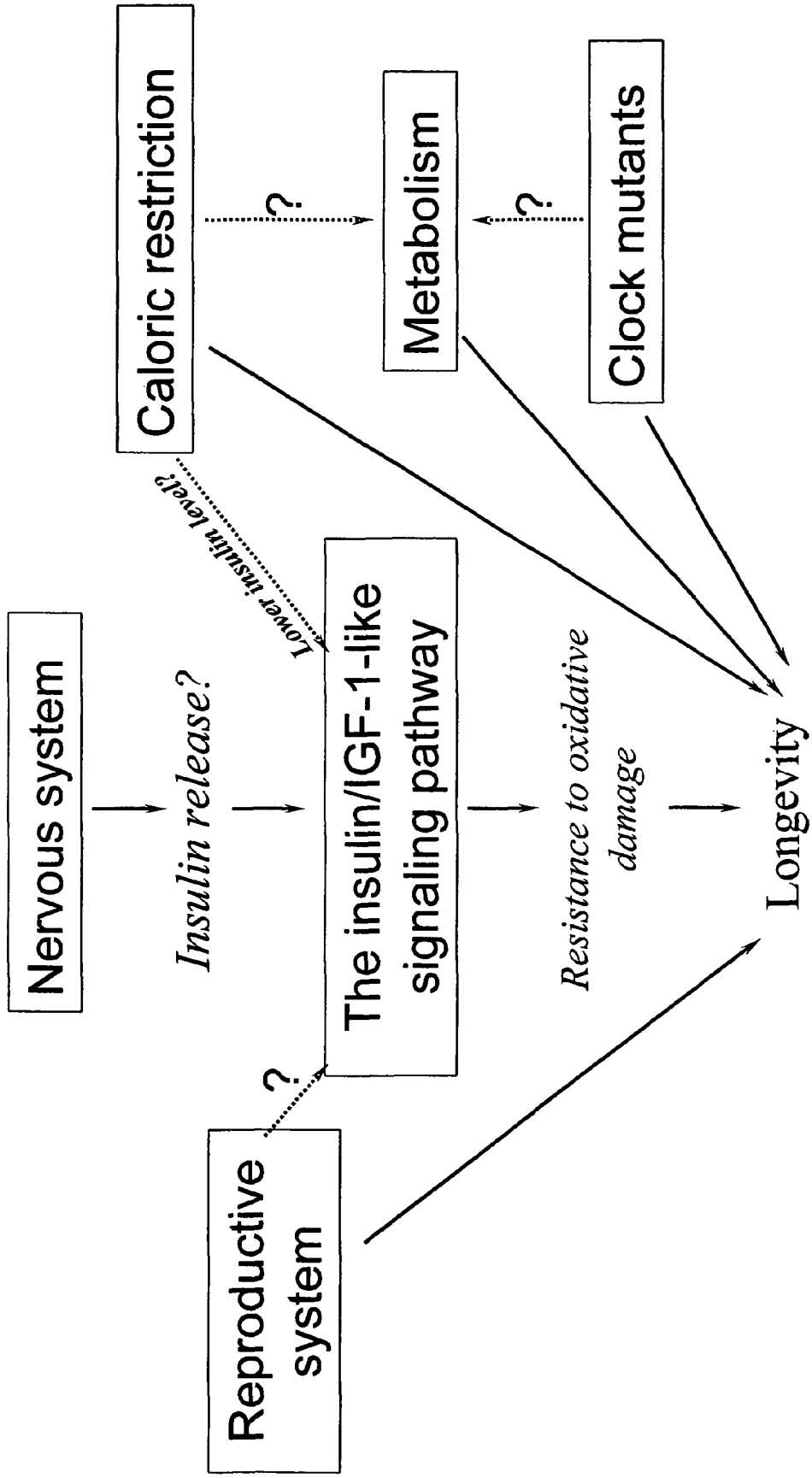
FIG. 20 is a schematic representation of various pathways affecting longevity.

The term "neurotransmitter signaling pathway" or "neuromodulatory pathway" refers to a signaling pathway involving proteins (e.g., enzymes) and other non-protein molecules (e.g., precursors, substrates, intermediates or products) utilized in transmission of an intracellular signal from a cell membrane (e.g., from a cell surface receptor) in order to control neurotransmitter release from a presynaptic terminal. FIG. 1 and FIG. 19 include schematic representations of neurotransmitter signaling pathways.

The term "insulin signaling pathway" (or "insulin-like signaling pathway") refers to the signaling pathway involving proteins (e.g., enzymes) and other non-protein molecules (e.g., precursors, substrates, intermediates or products) utilized in transmission of an intracellular signal from a cell membrane to the nucleus, in particular, from an insulin receptor (IR) or insulin-like growth factor (IGF) receptor at the cell surface to the nucleus. Additional signaling molecules in the insulin signaling pathway in mammals, for example, include insulin receptor substrate (IRS), phosphatidylinositol 3-kinase (PI3-K), phosphatase and tensin homologue deleted on chromosome ten (PTEN phosphatase), phosphoinositide kinase 1 (PDK1), protein kinase B (PKB) and forkhead transcription factors (FKHR). Such signaling molecules in *C. elegans*, for example, include IST-1, DAF-2, AAP-1, AGE-1, PDK-1, AKT-1, DAF-18 and DAF-16 (and the corresponding genes encoding these molecules, i.e., ist-1, daf-2, aap-1, age-1, pdk-1, akt-1, akt-2, daf-18, and daf-16, respectively). FIG. 1B includes a schematic representation of the insulin signaling pathway.

The term "deregulated" or "deregulation" includes the alteration or modification of at least one molecule in a signaling pathway, such that signal transmission by the pathway is altered or modified. Preferably, the activity or expression of at least one enzyme in the pathway is altered or modified such that signal transmission by the pathway is altered or modified.

The term "upmodulated" refers to an increase or enhancement of the activity or expression of a signaling pathway molecule. The term "downmodulated" refers to a decrease or inhibition of the activity or expression of a signaling pathway molecule.

"Impaired neurotransmitter signaling" refers to genetic or other alterations or modifications of at least one molecule in the neurotransmitter signaling pathway that lead to reduced activity in the neurotransmitter signaling pathways in mammals, organisms, cells, etc. These alterations include, but are not limited to, inhibition of expression or activity of signaling molecules involved in neurotransmitter signaling in mammals, organisms, cells, etc.

"Impaired insulin signaling" refers to genetic or other alterations that lead to reduced activity in the insulin or insulin-like signaling pathway in mammals, organisms, cells, etc. These alterations include, but are not limited to, inhibition of expression or activity of signaling molecules involved in insulin signaling in mammals, organisms, cells, etc.

"Increased activity" or "enhanced activity" of a signaling molecule refers to increased transcription or translation of the gene encoding the signaling molecule, increased activation of the signaling molecule, or increased activity of the signaling molecule, e.g., leading to increased activation of a target protein. Increased activity of DAF-16 or a DAF-16 orthologue, for example, refers to increased daf-16 or daf-16 orthologue transcription or translation, increased DAF-16 or DAF-16 orthologue activation and/or increased target protein activation.

A "target protein" of DAF-16 or a DAF-16 orthologue refers to any protein to which DAF-16 or a DAF-16 orthologue binds directly in order to modulate, or any protein whose transcription or translation is modulated by the binding of DAF-16 or a DAF-16 orthologue to a regulatory region of the gene or the mRNA encoding the protein. Target proteins can include, but are not limited to, HSP70, HSP90, catalase, ubiquitin and/or superoxide dismutase.

"Candidate agents" or "candidate molecules" means agents or molecules that can be tested in screening assays for suitability as agents to extend life span or to treat disorders, e.g., metabolic disorders, e.g., diabetes, e.g., type II diabetes. Typically, candidate agents are small molecules, peptides, oligonucleotides and/or derivatives thereof, or other compounds known to be useful as screening candidates in the drug discovery field.

As used herein, the term "agent" means a biological or chemical compound such as a simple or complex organic or inorganic molecule, a peptide, protein, oligonucleotide, polynucleotide, carbohydrate, or lipoprotein. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. Compounds can be tested singly or in combination with one another.

The term "diabetes" or "diabetic disorder" or "diabetes mellitus," as used interchangeably herein, refers to a disease which is marked by elevated levels of sugar (glucose) in the blood. Diabetes can be caused by too little insulin (a chemical produced by the pancreas to regulate blood sugar), resistance to insulin, or both.

The term "type II diabetes" refers to a chronic, life-long disease that results when the body's insulin does not work effectively. A main component of type 2 diabetes is "insulin resistance," wherein the insulin produced by the pancreas cannot connect with fat and muscle cells to allow glucose inside to produce energy, causing hyperglycemia (high blood glucose). To compensate, the pancreas produces more insulin, and cells, sensing this flood of insulin, become even more resistant, resulting in a vicious cycle of high glucose levels and often high insulin levels.

The phrase "disorders associated with diabetes," as used herein, refers to conditions and other diseases which are commonly associated with or related to diabetes. Example of disorders associated with diabetes include, for example, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, and osteoporosis.

As used herein, "expression" refers to the process by which polynucleotides are transcribed into mRNA and translated into peptides, polypeptides, or proteins.

An agent that "modulates" life-extension is an agent that affects life-extension, or lifespan, whether directly or indirectly, whether negatively or positively.

Various aspects of the invention are described in further detail in the following subsections.

I. Insulin-Like Signaling Pathway

The main pathway regulating life span in *C. elegans* is an insulin-like signaling pathway. Interestingly, several of the genes in this pathway were first isolated based on their effects on development. The normal lifecycle of *C. elegans* follows development from an egg, through four larval stages, and a final molt into a fertile, adult hermaphrodite. When nutrition is low or population density is high, the worms can undergo an alternative developmental program to form "dauer" larvae (Cassada R. C. & Russell R. (1975) *Dev. Biology* 46:326-342). The dauer larvae is a diapause stage that does not feed or reproduce, is stress resistant and is apparently non-aging, wherein worms can remain as dauer larvae for months (Klass M. R. & Hirsh D. I. (1976) *Nature* 260:523-525). When conditions improve, worms can re-enter the life cycle and develop into a normal reproductive hermaphrodite. The dauer formation genes (daf) were first isolated on the basis that they promote dauer arrest under plentiful growth conditions (dauer constitutive) or prevent dauer formation under crowded conditions (dauer defective) (Riddle D. L. et al. in *C. elegans* II, (1997) 739-768, Cold Spring Harbor Laboratory Press). Several of these genes, including daf-2, age-1 and daf-16, were subsequently identified as part of an insulin-like signaling pathway and shown to regulate life span.

The insulin-like signaling pathway in *C. elegans* contains 37 family members, of which daf-2 is the only insulin receptor-like gene (Pierce S. B. et al. (2001) *Genes and Dev.* 15:672-686; Gregoire F. M. et al. (1998) *Biochem. Biophys. Res. Com.* 249:385-390). DAF-2 resembles both insulin receptor (IR) and the related insulin growth factor-1 receptor (IGF1-R) (Kimura K. et al. (1997) *Science* 277:942-946). Activation of DAF-2 by an as yet unidentified ligand leads to activation of PI-3 kinase, the catalytic subunit of which is encoded in *C. elegans* by the age-1 gene (Morris J. Z. et al. (1996) *Nature* 382:536-539). Decrease-in-function mutations in either daf-2 or age-1 result in many phenotypes including constitutive dauer formation during development, resistance to stresses, and extension of life span in adults (Lithgow G. J. et al., (1994) *J. Gerontol.* 49:B270-276; Lithgow G. J. et al., (1995) *PNAS USA* 92:7540-4; Murakami S. & Johnson T. E. A *Genetics* 143:1207-1218; Honda Y. & Honda S., (1999) *FASED J* 13:1385-1393; Baryste D., (2001) *FASEB J* 15:627-634; Friedman D. B. & Johnson T. E., (1988) *Genetics* 118:75-86; Klass M. R., (1983) *Mech of Ageing and Dev.* 22:279-286). Activation of PI-3 kinase results in the generation of the 3-phosphoinositide second messengers PIP2 and PIP$_3$, which in turn activate the downstream kinases PDK-1, AKT-1, and AKT-2. These kinases ultimately antagonize the final output of the pathway, DAF-16, a homolog of the HNF-3/forkhead transcription factors (Kimura K. et al. (1997) *Science* 277:942-946; Ogg S. et al. (1997) *Nature* 389:994-9; Lin K. et al. (1997) *Science* 278:1319-1322). Null mutations of daf-16 decrease life span and completely suppress all phenotypes in double mutant combinations with daf-2 or age-1. The final targets of DAF-16 remain unknown but are presumed to regulate metabolism and fat storage (Kimura K. et al. (1997) *Science* 277:942-6; Lithgow G. J. et al. (1995) *PNAS USA* 92:7540-4).

In one study, the targeted neuronal expression of the daf-2 wild-type gene in daf-2 mutants was found to restore wild-type life span (C. A. Wolkow et al., (2000) *Science* 290 (5489):147-150). This result suggested that the DAF-2 function that is involved in regulation of life span could be associated specifically with neurons.

Importantly, the influence of the insulin/IGF signaling pathway on lifespan has been conserved across large evolutionary distances. For example, in the fruit fly *Drosophila*, reduced insulin/IGF signaling also mediates life-span extensions (Clancy D. J. (2001) *Science* 292:104-106; Tatar M. & Yin C. (2001) *Exp. Gerontol.* 36:723-738). This conservation indicates that information on the aging of simple animals is likely to be similarly important for mammalian aging.

II. Neurotransmitter Signaling Pathways

A. Synaptic Release of Neurotransmitters

In nerve cells, synaptic vesicles are the key cellular organelles involved in release of neurotransmitters at synapses. One important example of a neurotransmitter is the neuromuscular transmitter for locomotion, acetylcholine. Synaptic vesicles pass through a complex cycle of membrane fusion and fission reactions that govern the neurotransmitter release process (Brose et al., 2000 *Curr. Opin. Neurobiol.* 10:303-311; J. E. Richmond & K. S. Broadie, 2002 *Curr. Opin. Neurobiol.* 12:499-507). Vesicles are first loaded with transmitter, then translocate to the plasma membrane and dock at the active zone. Docked vesicles must then mature to a fusion competent state, a step referred to as "priming", before a rise in the intracellular $Ca^{2+}$ concentration can trigger fusion and transmitter release. Priming appears to be an essential and rate-limiting step in exocytosis, and in most synapses, priming is absolutely dependent on the presence of UNC-13 or the mammalian UNC-13 homologs. Studies indicate that UNC-13 regulates a step in the synaptic vesicle cycle that follows docking but precedes fusion (I. Augustin et al., 1999 *Nature* 400:457-561; J. E. Richmond et al. 1999 *Nat Neurosci* 2:959-964; B. Aravamudan et al., 1999 *Nat Neurosci* 2:965-971). Finally, the pool of synaptic vesicles are replenished by retrieving vesicle components through endocytosis.

In *C. elegans*, there are at least two UNC-13 variants that are expressed specifically in the nervous system and localized primarily in the neuromuscular junction. Mammals have at least three different Munc13 genes, Munc13-1, Munc13-2, and Munc13-3, of which MUNC13-1 and MUNC13-3 are specifically localized to presynaptic terminals. The unc-13 gene family possesses two conserved regions, the C1- and the C2-domains, as well as a calmodulin-binding site. The C2-domain meets the structural requirements to form a $Ca^{2+}$ binding site, although the mammalian homologs do not appear to bind $Ca^{2+}$, suggesting that unc-13 homologs do not function as exocytotic $Ca^{2+}$ sensors. The C1-domain is also found in Protein Kinase-C (PKC), and C1 serves in both proteins as a receptor for diacylglycerol (DAG) and phorbol ester. Binding of UNC-13 or PKC to DAG mediates their recruitment from the cytoplasm to the plasma membrane, ultimately leading to enhanced neurotransmitter release. UNC-13 and PKC thus act as parallel targets of the DAG second-messenger pathway (See FIG. 1).

What is the precise role of UNC-13 in mediating the priming event? Six different binding proteins of UNC-13/MUNC 13 have been identified, including syntaxin, UNC-18, the synaptic vesicle protein DOC2α, the brain-specific spectrin β-spIIIΣ, a GDP/GTP exchange factor MSEC7-1, and calmodulin. Of particular interest, syntaxin, an integral plasma membrane protein, forms the trimeric complex Soluble N-ethylmaleimide Sensitive Factor Attachment Receptor (SNARE) together with the plasma membrane protein SNAP-25 and the synaptic vesicle protein synaptobrevin/VAMP (R B Sutton et al., 1998 *Nature* 395:347-353). Stable assembly of SNARE is believed to drive membrane fusion and neurotransmitter release. Syntaxin is prevented from forming this complex when bound to UNC-18, another presynaptic protein that, like UNC-13, was first cloned from a *C. elegans* mutant based on its uncoordinated phenotype. Studies indicate that UNC-13, upon interaction with UNC-18, functions to remove UNC-18 and allow syntaxin to participate in SNARE complex formation. Thus UNC-13 and its mammalian orthologue is believed to exert its priming role by promoting SNARE complex assembly.

B. Neuromodulatory Signaling Pathways

In *C. elegans*, the release of acetylcholine from motor neurons is modulated by two competing mechanisms, an excitatory cholinergic pathway and an inhibitory serotonergic pathway. Significant molecular details of these two pathways are known (K G Miller et al., 1999 Neuron 24:323-333; S. Nurrish et al., 1999 Neuron 24:231-242; M R Lackner et al., 1999 Neuron 24:334-346). Cholinergic control is executed by the activation of muscarinic membrane receptors, which are positively coupled to phospholipase C$\beta$ (PLC$\beta$) via the G-protein G$\alpha$q. An increase in PLC$\beta$ activity leads to increased production of DAG, which in turn causes increases in transmitter relase via a mechanism dependent on UNC-13 proteins. Likewise, inhibitory serotonergic regulation occurs via G$\alpha$o-coupled serotonin receptors, although the precise mechanism by which G$\alpha$o decreases DAG levels is unclear. Thus, UNC-13 is a functional target of two converging DAG signaling cascades in neurons. Either activation of the cholinergic pathway or inhibition of the serotinergic pathway leads to increases in synaptic DAG levels and consequent increases in transmitter release. Importantly, all components of the two pathways are also present in mammals, suggesting the evolutionary conservation of DAG second-messenger pathways involving unc-13 and its mammalian homologs (N. Brose et al., 2000 Curr. Opin. Neurobiol. 10:303-311).

C. GABA Signaling

The amino acid gamma-aminobutyric acid (GABA) was first identified over half a century ago, and has long been considered to be the main inhibitory neurotransmitter in the adult mammalian brain. GABA is synthesized in neurons from glutamate in a reaction that is catalyzed by two glutamic acid decarboxylase (GAD) enzymes, GAD65 and GAD67. GABA is loaded into synaptic vesicles by a vesicular neurotransmitter transporter (VGAT) and is released from nerve terminals by calcium-dependent exocytosis. Non-vesicular forms of GABA secretion, however, have also been described. Upon crossing the synapse, the effects of GABA can be mediated by the activation of either ionotropic or metabotropic receptors. Ionotropic is a term that describes a receptor that exerts its effects through the modulation of ion channel activity. By contrast, a metabotropic receptor exerts its effects through enzyme activation. These receptors activated by GABA can be localized either in presynaptic or postsynaptic cells. GABA signals are terminated by reuptake of GABA into nerve terminals and/or into surrounding glial cells by a class of plasma-membrane GABA transporters (GASTs). Thereafter, GABA is metabolized by a transamination reaction catalyzed by GABA transaminase (GABA-T).

The two main subtypes of GABA receptors are $GABA_A$ and $GABA_B$. $GABA_A$ receptors generally mediate fast responses, while $GABA_B$ receptors mediate slow responses. $GABA_A$ receptors are members of the ligand-gated ion channel superfamily that includes nicotinic acetylcholine receptors, glycine receptors and the serotonin 5-HT receptor. For this class of receptors, ligand binding is followed by a conformational change in the channel protein that allows a net inward or outward flow of ions through the membrane-spanning pore of the channel. $GABA_A$ receptors carry primarily chloride ions, and synaptic inhibition via these receptors can occur either presynaptically or postsynaptically. In contrast, $GABA_B$ is a metabotropic receptor, and signalling by this receptor occurs through the activation of heterotrimeric G proteins. G proteins transduce signals through the positive or negative regulation of primary effectors, second messengers and their associated enzymes, which can, in turn, modulate channel and receptor function. $GABA_B$ receptors are localized both presynaptically and postsynaptically, and they use different mechanisms at these locations to regulate cell excitability. Presynaptic inhibition occurs through a reduction in calcium current at the nerve terminal and a subsequent reduction in transmitter release, whereas postsynaptic inhibition occurs by activation of potassium currents that hyperpolarize the neuron.

III. Screening Assays

The methods of the invention are suitable for use in methods to identify and/or characterize potential pharmacological agents, e.g. identifying new pharmacological agents from a collection of test substances, in particular, pharmacological agents for use in increasing life span and/or enhancing quality of life in aged individuals. Pharmacological agents identified according to the methodologies of the invention are also useful, for example, in enhancing stress resistance in individuals, and increasing the cytoprotective abilities of cells.

The methods described herein are in vitro and in vivo cell- and animal (e.g., nematode)-based screening assays.

A. Screening in Whole Organisms

The invention provides screening assays in whole organisms. In the whole organism-based embodiments, whole organisms comprising the organism having a deregulated neurotransmitter signaling pathway and/or insulin signaling pathway are used for testing agents.

The invention provides a method for identifying an agent capable of enhancing longevity, comprising: (a) contacting an organism having a deregulated neurotransmitter signaling pathway with a test agent, wherein a detectable phenotype is associated with the deregulated neurotransmitter signaling pathway; and (b) assaying for the ability of the test agent to effect said phenotype, wherein the agent is identified based on its ability to alter said phenotype as compared to a suitable control. A variation on this method comprises (a) contacting an organism further having a deregulated insulin signaling pathway, wherein said detectable phenotype is associated with said deregulated neurotransmitter signaling pathway and said deregulated insulin signaling pathway, and (b) assaying for the ability of the test agent to effect said phenotype, wherein the agent is identified based on its ability to alter said phenotype as compared to a suitable control. In one embodiment, the deregulated insulin signaling pathway molecule is selected from the group consisting of DAF-2, IST-1, AAP-1, AGE-1, PDK-1, AKT-1, AKT-2 and DAF-18, or a mammalian orthologue thereof. In another embodiment, the deregulated neurotransmitter signaling pathway molecule is selected from the group consisting of muscarinic receptor, EGL-30, EGL-8, serotonin receptor, CAT-1, GOA-1 and DGK-1, UNC-13, PKC, UNC-18, UNC-64, SNAP-25, synaptobrevin and UNC-31.

In one embodiment, the organism is a nematode. In a preferred embodiment of the invention, the roundworm *Caenorhabditis elegans* is employed. *C. elegans* is a simple soil nematode species that has been extensively described at the cellular and molecular level, and is a model organism for biological studies. *C. elegans* can develop through a normal life cycle that involves four larval stages and a final molt into an adult hermaphrodite. The dauer pathway is an alternative life cycle stage common to many nematode species which is normally triggered by environmental stresses such as starvation, temperature extremes, or overcrowding. Genetically, the dauer pathway has been most intensively studied in *C. elegans*. The response to overcrowding in *C. elegans* is mediated by a substance known as dauer pheromone, which is secreted by the animals. When dauer pheromone becomes sufficiently concentrated, it triggers commitment to the dauer alternative life cycle stage. A strong correlation exists between a constitutive dauer and the long-lived phenotype.

In preferred embodiments of the invention, the detectable phenotype is increased or decreased life span. In another embodiment, the detectable phenotype is constitutive dauer formation or defective dauer formation. In other embodiments, the phenotype is increased or decreased body size, or increased or decreased stress resistance, wherein stress resistance is selected from, but not limited to, the group consisting of oxidative stress, ultraviolet (UV) stress, hypoxic stress, heavy metal stress and heat stress.

When screening for an effect of dauer formation, the assay population of C. elegans is preferably exposed to test agent during the portion of the life cycle at which commitment to the dauer pathway is made. Measurement of dauer formation has been previously described. See e.g., Riddle et al., Genetic and Environmental Regulation of Dauer Larva Development, In Riddle, Blumenthal, Meyer, and Priess (eds), C. ELEGANS II., Cold Spring Harbor Laboratory Press, Cold Spring Harbor, N.Y. (1997). In mutant strains containing deregulated JNK and/or insulin signaling and exhibiting a constitutive dauer phenotype, an agent is identified based on its ability to reverse that phenotype.

Life span assays have also been well described (Apfeld J. & Kenyon C. (1998) Cell 95: 199-210). In strains that exhibit an extended life span phenotype, an agent is identified, for example, based on its ability to either further extend or shorten the lifespan. Stress resistance assays are also well known to those skilled in the relevant art. For example, resistance to ultraviolet (UV) stress is determined by exposing the organism to UV light and measuring life span from the day of UV treatment. Oxidative stress resistance is determined, for example, by exposing the animals to paraquat, which produces superoxide when taken up by cells, and determining survival from the day of treatment (Feng et al. (2001) Dev. Cell 1:1-20.). Heat tolerance is measured, for example, by exposing adult animals to a 35° C. heat shock for 24 hours, and then scoring the animals for viability.

In assay formats featuring indicator phenotypes, the phenotype of the animals may be detected by direct observation. An alternative to direct observation is mechanical detection of the animals. For instance, such detection could involve the determination of optical density across the test surface by a machine. The animals would be detected by changes in density at the location where an animal was located.

Alternatively, if the animals are expressing a reporter gene that can be detected in living animals, e.g., green fluorescent protein (GFP), a machine could monitor the animals using a suitable reporter gene detection protocol.

If desired, additional tests may be conducted using the agent identified to further characterize the nature of the agent's function with respect to longevity. For example, egg laying may also be measured to determine whether the longevity occurs by delaying maturity. As another example, other phenotypes associated with other gerontogenes could be tested to determine whether the identified agent affects functional pathways associated with these other genes.

Another embodiment of the invention provides a method for identifying an agent capable of enhancing longevity, comprising: contacting an organism with a test agent, said organism having a neurotransmitter signaling pathway; assaying for the ability of the test agent to affect an indicator of said neurotransmitter signaling pathway, wherein the agent is identified based on its ability to alter said indicator as compared to a suitable control. Another embodiment of the invention provides a method for identifying an agent capable of enhancing longevity, comprising contacting an organism with a test agent, said organism having a neurotransmitter signaling pathway and an insulin signaling pathway; assaying for the ability of the test agent to affect at least one indicator of neurotransmitter signaling or insulin signaling, wherein the agent is identified based on its ability to alter said indicator as compared to a suitable control.

In such assays of the invention, the organism is a nematode. In a preferred embodiment, the nematode is C. elegans. In a further embodiment, the organism is a parasitic nematode.

In such assays, indicators can be any molecule of the neurotransmitter or insulin-like signaling pathways, or any molecule known to be a target or substrate of said signaling pathway molecules. In one embodiment, the indicator is selected from, but not limited to, the group consisting of DAF-16, superoxide dismutase (SOD), glucose transporter 4 (GLUT4) and glucose transporter 1 (GLUT1). Recent publications indicate that two other members of the insulin-like signaling pathway in C. elegans, DAF-9 and DAF-12, function downstream of DAF-16 (Gerisch B. et al. (2001) Dev. Cell, 1(6):841-51; Jia K. et al. (2002) Development 129:221-231). In C. elegans, daf-9 encodes a cytochrome P450 related to vertebrate steroidogenic hydroxylases, suggesting it could metabolize a DAF-12 ligand. In another embodiment, therefore, the indicator may be either DAF-9 or DAF-12.

In such an assay, the agent may be identified based on its ability to increase or decrease the indicator. The agent may alter expression of the indicator, wherein the expression is nucleic acid expression or polypeptide expression. The alteration of expression may be a change in the rate of expression or steady state expression.

In one embodiment, the agent alters the activity of the indicator. In a preferred embodiment, the agent may alter the post-translational modification state of the indicator, e.g. the phosphorylation state of the indicator. Techniques are well known in the art for analyzing phosphorylation and other post-translational modification states. For example, phosphorylation may be determined by the use of antibodies to phospho-epitopes to detect a phosphorylated polypeptide by Western analysis.

In another embodiment, the agent may alter the cellular localization of the indicator, such as from cytoplasmic to nuclear. Changes in cellular localization can be determined by introducing a chimeric form of the indicator containing a reporter gene. Plasmid constructs can be introduced into C. elegans using described transformation methods. See e.g., Mello et al., (1991) EMBO J 10:3959-3970. Preferably, the plasmid constructs are linear constructs. An important aspect of transformation in C. elegans is that plasmid constructs can be easily cotransformed, thus allowing for assay formats in which C. elegans are engineered to express, for example, non-C. elegans signaling pathway molecules and reporter genes. Preferably, a reporter gene is used that can be scored in a living animal, but does not affect the indicator phenotype of the animal. For example, green fluorescent protein (herein referred to as "GFP") is a widely used reporter molecule in living systems. Ellenberg (1999) Trends Cell Biol. 9:52-56; Chalfie et al., (1994) Science 263:802-805.

In other embodiments, the indicator is any one of the following: nucleic acid expression, polypeptide expression, rate of expression, and steady state expression. In particular embodiments, the indicator is any one of the following: acetylcholine, UNC-13, DAG, concentration of $Ca^{2+}$, DAF-16, SOD and glucose transporter.

In other embodiments, the agent is identified based on its ability to: alter the level of said indicator, alter the activity of said indicator, alter an interaction of said indicator, alter localization of said indicator, alter the synaptic release of said indicator, or alter the post-translational modification state of said indicator. In still other embodiments, the alteration of said indicator is an increase or a decrease in said indicator.

B. Cell-Based Screening Assays

The invention further features cell-based assays for the identification of an agent capable of enhancing longevity. In one embodiment, the invention provides methods for identifying an agent that enhances longevity, comprising contacting a cell with a test agent, said cell having a neurotransmitter signaling pathway, and detecting an indicator of said neurotransmitter signaling pathway, wherein an agent is identified based on its ability to modulate the neurotransmitter signaling pathway in said cell.

The invention further provides a method for identifying an agent that enhances longevity, comprising contacting a cell with a test agent, said cell having a neurotransmitter signaling pathway and an insulin signaling pathway, and detecting an indicator of said neurotransmitter signaling pathway or insulin signaling pathway; wherein an agent is identified based on its ability to modulate the neurotransmitter signaling pathway or insulin signaling pathway in said cell.

The invention still further provides a method for identifying an agent that enhances longevity, comprising contacting a cell population with a test agent, said population comprising a cell having a neurotransmitter signaling pathway and a cell having an insulin signaling pathway, and detecting an indicator of the neurotransmitter signaling pathway or insulin signaling pathway, wherein an agent is identified based on its ability to modulate the neurotransmitter signaling pathway or insulin signaling pathway in said cell.

The cell-based screening assays described herein have several advantages over conventional drug screening assays: 1) if an agent must enter a cell to achieve a desired therapeutic effect, a cell-based assay can give an indication as to whether the agent can enter a cell; 2) a cell-based screening assay can identify agents that, in the state in which they are added to the assay system are ineffective to modulate the neurotransmitter and/or insulin signaling polynucleotide and/or polypeptide function, but that are modified by cellular components once inside a cell in such a way that they become effective agents; 3) most importantly, a cell-based assay system allows identification of agents affecting any component of a pathway that ultimately results in characteristics that are associated with neurotransmitter and/or insulin signaling polynucleotide and/or polypeptide function.

In one embodiment, suitable host cells include, but are not limited to, fungi (including yeast), bacterial, insect and mammalian cells. In a preferred embodiment, the host cell is a human cell or is derived from a nematode, e.g., C. elegans.

In one embodiment of the cell-based methods, the cell population comprises both presynaptic cells and postsynaptic cells. In a preferred embodiment, the presynaptic cells are nerve cells. In another preferred embodiment, the postsynaptic cells are nerve cells. In yet another preferred embodiment, the postsynaptic cells are muscle cells.

In preferred embodiments of the cell-based methods, the indicator is presynaptic localization of a neurotransmitter signaling pathway molecule, release of a neurotransmitter, or release of insulin.

In other embodiments, the indicator is selected from the group consisting of acetylcholine, diacylglycerol (DAG), SNARE complex, and UNC-13 or a mammalian orthologue thereof.

In other embodiments, the indicator is any one of the following: conversion of substrate to corresponding product catalyzed by a downstream enzyme in said pathway; activation or inhibition of a downstream enzyme in said pathway; a transcriptional event regulated by said pathway, e.g., when the transcriptional event is expression of a nuclear factor regulated by said pathway; and activation or inhibition of a transcription factor regulated by said pathway.

In other embodiments, the indicator is selected from the group consisting of DAF-16, superoxide dismutase (SOD), and glucose transporters.

In still other embodiments, the indication involves an endogenous gene or protein, or a reporter gene or protein.

In the cell-based methods of the present invention, the indicator of the neurotransmitter signaling and/or insulin signaling may include a neurotransmitter signaling and/or insulin signaling polynucleotide and/or polypeptide. Characteristics associated with said neurotransmitter signaling and/or insulin signaling polynucleotide and/or polypeptide depend upon the polynucleotide or polypeptide. Functional characteristics include, but are not limited to, transcription, translation (including levels of precursor and/or processed polypeptide), location of protein product (such as nuclear or membrane localization), post-translational modification of protein product (such as phosphorylation or acetylation), any enzymatic activities, such as kinase activity, structural and/or functional phenotypes (such as stress resistance or life cycle), and expression (including repression or de-repression) of any other genes known to be controlled (modulated) by the polynucleotide. Any measurable change in any of these and other parameters indicate that the agent may be useful. In a preferred embodiment, given that neurotransmitter and/or insulin signaling pathway molecules that regulate longevity have been identified by their ability to confer life extension when their function is reduced, useful agents will preferably be agents that confer decreased functionality.

Modulation of function of a neurotransmitter signaling pathway molecule, polynucleotide and/or polypeptide, may occur at any level. An agent may modulate function by reducing or preventing transcription of a neurotransmitter signaling pathway polynucleotide. An example of such an agent is one that binds to the upstream controlling region, including a polynucleotide sequence or polypeptide. An agent may modulate translation of mRNA. An example of such an agent is one that binds to the mRNA, such as an anti-sense polynucleotide, or an agent which selectively degrades or stabilizes the mRNA. An agent may modulate function by binding to the neurotransmitter signaling pathway polypeptide. An example of such an agent is a polypeptide or a chelator.

In preferred embodiments, to identify agents that inhibit neurotransmitter and/or insulin signaling, the skilled artisan could look for conversion of a substrate to the corresponding product catalyzed by a downstream enzyme in the signaling pathway. The artisan could look for activation or inhibition of a downstream enzyme in the pathway, for example the activation of downstream kinase in the neurotransmitter or insulin-like signaling pathway. The artisan could further look for an alteration of a transcriptional event regulated by the pathway, such as the expression of a nuclear factor regulated by the pathway. Another indicator may be the activation or inhibition of a transcription factor regulated by the pathway. In each of these instances, the indication may involve an endogenous gene or protein. Alternatively, the indication could involve a reporter gene or protein.

Measuring all of these parameters (such as those using reporter genes) involve methods known in the art and need not be discussed herein. For example, degree of transcription can be measured using standard Northern analysis. Amount of expression product may be measured simply by Western analysis (if an antibody is available) or by a functional assay that detects the amount of protein, such as kinase activity.

Cell-based screening assays of the present invention can be designed, e.g., by constructing cell lines or strains of animals in which the expression of a reporter protein, i.e., an easily assayable protein, such as β-galactosidase, chloramphenicol acetyltransferase (CAT), green fluorescent protein (GFP) or luciferase, is dependent on neurotransmitter and/or insulin signaling polynucleotide and/or polypeptide function. The cell is exposed to a test agent, and, after a time sufficient to effect β-galactosidase expression and sufficient to allow for depletion of previously expressed β-galactosidase, the cells are assayed for the production of β-galactosidase under standard assaying conditions.

Reporter genes include, but are not limited to, alkaline phosphatase, chloramphenicol acetyl transferase, galactosidase, luciferase and green fluorescent protein. Identification methods for the products of reporter genes include, but are not limited to, enzymatic assays and fluorimetric assays. Reporter genes and assays to detect their products are well known in the art and are described, for example in Current Protocols in Molecular Biology, eds. Ausubel et al., Greene Publishing and Wiley-Interscience: New York (1987) and periodic updates. Reporter genes, reporter gene assays and reagent kits are also readily available from commercial sources (Stratagene, Invitrogen and etc.).

Introduction of neurotransmitter and/or insulin signaling polynucleotides (or reporter gene polynucleotides) depend on the particular host cell used and may be by any of the many methods known in the art, such as microinjection, spheroplasting, electroporation, CaCl, precipitation, lithium acetate treatment, and lipofectamine treatment.

Polynucleotides introduced into a suitable host cell(s) are polynucleotide constructs comprising a neurotransmitter and/or insulin signaling polynucleotide. These constructs contain elements (i.e., functional sequences) which, upon introduction of the construct, allow expression (i.e., transcription, translation, and post-translational modifications, if any) of neurotransmitter and/or insulin signaling polypeptide amino acid sequence in the host cell. The composition of these elements will depend upon the host cell being used. For introduction into *C. elegans*, polynucleotide constructs will generally contain the neurotransmitter and/or insulin signaling polynucleotide operatively linked to a suitable promoter and will additionally contain a selectable marker such as rol-6 (su1006). Other suitable host cells and/or whole animals include *Drosophila*, yeast and mammalian cells. Suitable selectable markers for nematode cells are those that enable the identification of cells that have taken up the nucleic acid, such as morphologic and behavioral markers such as rol-6 or visual markers such as green fluorescent protein. Screening of the transfectants identifies cells or animals that have taken up and express the polynucleotide.

In some embodiments, a neurotransmitter and/or insulin signaling polynucleotide is operatively linked to an inducible promoter. Use of an inducible promoter provides a means to determine whether the agent is acting via a pathway involving the neurotransmitter and/or insulin signaling polynucleotide. If an agent modulates a functional characteristic of a neurotransmitter and/or insulin signaling polynucleotide and/or polypeptide in a cell in which the inducible promoter is activated, an observation that the agent fails to elicit the same result in a cell in which the inducible promoter is not activated indicates that the agent is affecting at least one step or aspect of neurotransmitter and/or insulin signaling polynucleotide function. Conversely, if the functional characteristic is also observed in a cell in which the inducible promoter is not activated, then it can be assumed that the agent is not necessarily acting solely via the neurotransmitter and/or insulin signaling polynucleotide functional pathway.

C. In Vitro Screening Assays

In the in vitro embodiments, an agent is tested for its ability to modulate activity or expression of a neurotransmitter signaling pathway molecule using the methods described herein.

The invention provides an in vitro method of identifying an agent capable of enhancing longevity, comprising: contacting an assay composition with a test compound, wherein said assay composition comprises a neurotransmitter signaling pathway molecule, and detecting activity or expression of said neurotransmitter signaling pathway molecule, wherein said agent is identified based on its ability to modulate activity or expression of said neurotransmitter signaling pathway molecule.

In preferred embodiments, the assay composition comprises a cell-free extract or comprises purified proteins/components.

In preferred embodiments, the agent is identified based on its ability to inhibit activity or expression of said neurotransmitter signaling pathway molecule, or on its ability to enhance activity or expression of said neurotransmitter signaling pathway molecule.

In one embodiment, the neurotransmitter signaling pathway is cholinergic. Preferably, the molecule is selected from the group consisting of muscarinic receptors, EGL-30, EGL-8, and RIC-8, or a mammalian orthologue thereof.

In one embodiment, the neurotransmitter signaling pathway is serotinergic. Preferably, the serotinergic signaling pathway molecule is selected from the group consisting of serotonin receptors, CAT-1, GOA-1, DGK-1, EGL-10, or a mammalian orthologue thereof.

In one embodiment, the neurotransmitter signaling pathway is GABA signaling.

Preferably, the GABA signaling molecule is selected from the group consisting of UNC-25, UNC-47, and UNC-49, or a mammalian orthologue thereof.

In another embodiment, the agent is identified based on its ability to modulate an interaction of said neurotransmitter signaling pathway molecule.

In such an assay, the neurotransmitter signaling molecule may be a polynucleotide(s) or polypeptide(s). In such an assay, the neurotransmitter signaling molecule may be present as part of a cell-free extract or a partially purified system.

Alternatively, they may be purified or recombinant. The signaling pathway molecules to be used in these screening methods may be obtained using standard synthetic methods known in the art, including, but not limited to, isolation from natural sources, recombinant methods, chemical synthetic methods, and enzymatic digestion followed by purification.

The modulation of activity or expression of the neurotransmitter signaling molecules may be an increase or a decrease. In such an assay, the detection of the activity or expression of the neurotransmitter signaling molecules can be studied using standard techniques.

In preferred embodiments, an agent is screened in an in vitro screening assays, which may be any of the following: (1) an assay that determines whether an agent is modulating transcription of a neurotransmitter signaling pathway polynucleotide; (2) an assay for an agent which modulates translation of mRNA or polynucleotides encoding a neurotransmitter signaling pathway molecule; (3) an assay for an agent that binds to a neurotransmitter signaling pathway polynucleotide or polypeptide; (4) an assay for an agent that modulates post-translational modification of a neurotransmitter signaling polypeptide.

For an assay that determines whether an agent modulates transcription of a neurotransmitter signaling polynucleotide, an in vitro transcription or transcription/translation system may be used. These systems are available commercially, and generally contain a coding sequence as a positive, preferably internal, control. A neurotransmitter signaling polynucleotide is introduced and transcription is allowed to occur. Comparison to transcription products between an in vitro expression system that does not contain any agent (negative control) with an in vitro expression system that does contain the agent indicates whether an agent is affecting transcription. Comparison of transcription products between control and the neurotransmitter signaling polynucleotide indicates whether the agent, if acting on this level, is selectively affecting transcription of the neurotransmitter signaling polynucleotide (as opposed to affecting transcription in a general, nonselective or specific fashion).

For an assay that determines whether an agent modulates translation of a neurotransmitter signaling mRNA or a polynucleotide encoding a neurotransmitter signaling polypeptide, an in vitro transcription/translation assay as described above may be used, except the translation products are compared. Comparison of translation products between an in vitro expression system that does not contain any agent (negative control) with an in vitro expression system that does contain agent indicates whether an agent is affecting transcription. Comparison of translation products between control and the neurotransmitter signaling polynucleotide indicates whether the agent, if acting on this level, is selectively affecting translation of the neurotransmitter signaling polynucleotide (as opposed to affecting translation in a general, nonselective or unspecific fashion).

For an assay for an agent that binds to a neurotransmitter signaling polypeptide, a neurotransmitter signaling polynucleotide is first recombinantly expressed in a prokaryotic or eukaryotic expression system as a native or as a fusion protein in which a neurotransmitter signaling polypeptide (or fragment thereof) is conjugated with a well-characterized epitope or protein as are well known in the art. Recombinant neurotransmitter signaling polypeptide is then purified by, for instance, immunoprecipitation using anti-neurotransmitter signaling polypeptide antibodies or anti-epitope antibodies or by binding to immobilized ligand of the conjugate. An affinity column made of neurotransmitter signaling polypeptide or neurotransmitter signaling polypeptide fusion protein is then used to screen a mixture of compounds which have been appropriately labeled. Suitable labels include, but are not limited to flurochromes, radioisotopes, enzymes and chemiluminescent compounds. The unbound and bound compounds can be separated by washes using various conditions (e.g. high salt, detergent ) that are routinely employed by those skilled in the art. Non-specific binding to the affinity column can be minimized by pre-clearing the compound mixture using an affinity column containing merely the conjugate or the epitope. A similar method can be used for screening for agents that competes for binding to a neurotransmitter signaling polypeptide. In addition to affinity chromatography, there are other techniques such as measuring the change of melting temperature or the fluorescence anisotropy of a protein which will change upon binding another molecule. For example, a BIAcore assay using a sensor chip (supplied by Pharmacia Biosensor, Stitt et al. (1 995) Cell 80: 661-670) that is covalently coupled to native neurotransmitter signaling polypeptide or neurotransmitter signaling polypeptide fusion proteins, may be performed to determine the JNK or insulin signaling polypeptide binding activity of different agents.

In another embodiment, an in vitro screening assay detects agents that compete with another substance (most likely a polypeptide) that binds a neurotransmitter signaling polypeptide. Competitive binding assays are known in the art and need not be described in detail herein. Briefly, such an assay entails measuring the amount of neurotransmitter signaling polypeptide complex formed in the presence of increasing amounts of the putative competitor. For these assays, one of the reactants is labeled using, for example, $^{32}$P.

In another embodiment, an in vitro screening assay detects agents that modulate the post-translational modification of a polypeptide. For example, techniques can be used for studying phosphorylation of proteins (such as DAF-16) or acetylation of proteins by using antibodies to phospho-epitopes or acetyl group-epitopes.

It is also understood that the in vitro screening methods of this invention include structural, or rational, drug design, in which the amino acid sequence, three-dimensional atomic structure or other property (or properties) of a neurotransmitter signaling polynucleotide or polypeptide provides a basis for designing an agent which is expected to bind to a neurotransmitter signaling polynucleotide or polypeptide. Generally, the design and/or choice of agents in this context is governed by several parameters, such as the perceived function of the polynucleotide or polypeptide target, its three-dimensional structure (if known or surmised), and other aspects of rational drug design. Techniques of combinatorial chemistry can also be used to generate numerous permutations of candidate agents. For purposes of this invention, an agent designed and/or obtained by rational drug designed may also be tested in the cell-based assays described above.

The screening assay formats and components utilized in the screening assays featured in the instant invention are also useful for screening for agents that can be used to treat disorders, e.g., metabolic disorders, e.g., diabetes, e.g., type II diabetes. Type 2 diabetes is a disease of peripheral insulin resistance combined with pancreatic beta-cell dysfunction, and current evidence indicates that disruption of insulin/insulin-like growth factor (IGF)-1 signaling mechanisms may contribute to both defects. Based on the discoveries provided herein, which reveal that defects in neurotransmitter signaling pathways (e.g., the cholinergic, serotonergic and GABA signaling pathways) lead to modulation of lifespan in a mechanism dependent upon the insulin-like signaling pathway molecule DAF-16, components of these neurotransmitter signaling pathways and their downstream effector molecules are attractive therapeutic targets for treatment of metabolic disorders, e.g., diabetes, e.g., type 2 diabetes and disorders associated with diabetes. The skilled artisan will appreciate that assay formats or combinations of assay components as described herein may be modified for the above described purpose.

D. Test Compounds

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993)

*Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) *Science* 249:386-390); (Devlin (1990) *Science* 249:404-406); (Cwirla et al. (1990) *Proc. Natl. Acad Sci.* 87:6378-6382); (Felici (1991) *J. Mol. Biol.* 222:301-310); (Ladner supra.)).

In a preferred embodiment, the library is a natural product library, e.g., a library produced by a bacterial, fungal, or yeast culture. In another preferred embodiment, the library is a synthetic compound library.

E. Suitable Controls

Assay methods generally require comparison to a control sample to which no agent is added. The screening methods described above represent primary screens, designed to detect any agent that may exhibit anti-aging activity. The skilled artisan will recognize that secondary tests will likely be necessary in order to evaluate an agent further. For example, a cytotoxicity assay would be performed as a further corroboration that an agent which tested positive in a primary screen would be suitable for use in living organisms. Any assay for cytotoxicity would be suitable for this purpose, including, for example the MTT assay (Promega).

This invention further pertains to novel agents identified by the above-described screening assays. Accordingly, it is within the scope of this invention to further use an agent identified as described herein in an appropriate animal model, e.g., an animal model to determine the efficacy, toxicity, or side effects of treatment with such an agent.

III. Recombinant Cells and Organisms

Further encompassed in the instant invention are cells and organisms, e.g., recombinant cells and organisms, preferably including vectors or genes (e.g., wild-type and/or mutated genes) as described herein and/or cultured in a manner which results in the modulation, e.g., overexpression, of a neurotransmitter or insulin-like signaling pathway molecule. In one embodiment, a serotonergic signaling pathway molecule is overexpressed, e.g., serotonin receptor, CAT-1, GOA-1 and DGK-1, or a mammalian orthologue thereof. The term "recombinant" cell or organism includes a cell (e.g., mammalian cell or nematode cell) or organism (e.g., nematode, e.g., *C. elegans*) which has been genetically altered, modified or engineered (e.g., genetically engineered) such that it exhibits an altered, modified or different genotype and/or phenotype (e.g., when the genetic modification affects coding nucleic acid sequences of the cell or organism) as compared to the naturally-occurring cell or organism from which it was derived. Preferably, a "recombinant" cell or organism of the present invention has been genetically engineered such that it overexpresses at least one gene or gene product (e.g., a serotonergic signaling pathway gene or gene product) as described herein. The ordinary skilled will appreciate that a cell or organism expressing or overexpressing a gene product produces or overproduces the gene product as a result of expression or overexpression of nucleic acid sequences and/or genes encoding the gene product.

Suitable host cells and/or whole animals include, but are not limited to, for example, nematode (e.g., *C. elegans*), insect, yeast and mammalian cells. In one embodiment, the host cells and/or whole animals are not insects, e.g., *Drosophila*.

The term "overexpressed" or "overexpression" includes expression of a gene product (e.g., a serotonergic signaling pathway molecule, e.g., serotonin receptor, CAT-1, GOA-1 or DGK-1) at a level greater than that expressed prior to manipulation of the cell or organism or in a comparable cell or organism which has not been manipulated. In particular embodiments of the invention, overexpression is at least about 2, 3, 4, 5, 6, 7, 8, 9, 10, 11, 12, 13, 14, 15, 16, 17, 18, 19, 20, 25, 30, 40, 50 or more fold overexpression as compared to that expressed prior to manipulation of the cell or organism or in a comparable cell or organism which has not been manipulated.

In one embodiment, the cell or organism can be genetically manipulated (e.g., genetically engineered) to overexpress a level of gene product greater than that expressed prior to manipulation of the cell or organism or in a comparable cell or organism which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene routine in the art (including but not limited to use of antisense nucleic acid molecules, for example, to block expression of repressor proteins).

In another embodiment, the cell or organism can be physically or environmentally manipulated to overexpress a level of gene product greater than that expressed prior to manipulation of the cell or organism or in a comparable cell or organism which has not been manipulated. For example, a cell or organism can be treated with or cultured in the presence of an agent known or suspected to increase transcription of a particular gene and/or translation of a particular gene product such that transcription and/or translation are enhanced or increased. Alternatively, a cell or organism can be cultured at a temperature selected to increase transcription of a particular gene and/or translation of a particular gene product such that transcription and/or translation are enhanced or increased.

The term "deregulated" or "deregulation" includes the alteration or modification of at least one gene in a cell or organism that is involved in a signaling pathway, e.g., the neurotransmitter signaling pathway or the insulin-like signaling pathway, such that the signal transmission by the pathway is altered or modified. Preferably, the activity or expression of at least one enzyme in the pathway is altered or modified such that signal transmission by the pathway is altered or modified. In a particular embodiment, the methodologies of the present invention feature recombinant cells or organisms in which the activity or expression of a serotonergic neurotransmitter signaling pathway molecule, e.g., serotonin receptor, CAT-1, GOA-1, DGK-1 or a mammalian orthologue thereof, is increased. In a preferred embodiment, at least one gene that encodes a serotonergic signaling pathway molecule, e.g., serotonin receptor, CAT-1, GOA-1, DGK-1 or a mammalian orthologue thereof, is altered or modified such that the gene product is enhanced or increased. In one embodiment, a recombinant cell or organism is designed or engineered such that the activity or expression of a serotonergic signaling molecule, e.g., serotonin receptor, CAT-1, GOA-1, DGK-1 or a mammalian orthlogue thereof, is increased and the activity or expression of at least one cholinergic signaling molecule is decreased, e.g., inhibited.

Other preferred "recombinant" cells or organisms of the present invention have a deregulated insulin signaling pathway. In particular embodiments, at least one gene that encodes an insulin signaling pathway molecule, e.g., DAF-2, AAP-1, IRS, AGE-1, PDK-1, AKT-1, AKT-2, or DAF-18 or a mammalian orthologue thereof, is altered or modified such that the gene product is enhanced or increased. For example, in one embodiment, a recombinant cell or organism is designed or engineered such that the activity or expression of a serotonergic signaling molecule, e.g., serotonin receptor, CAT-1, GOA-1 and DGK-1, is increased and the activity or expression of at least one insulin signaling molecule is decreased, e.g., inhibited. In another embodiment, a recombinant cell or organism is designed or engineered such that the activity or expression of a cholinergic signaling molecule, e.g., muscarinic receptor, EGL-8, EGL-30, or a mammalian orthologue thereof, is decreased and the activity or expression of at least one insulin signaling molecule is decreased, e.g., inhibited.

IV. Methods of Treatment

The present invention provides methods of treating a subject in need thereof with an agent which modulates neurotransmitter signaling and/or insulin signaling, for example, an agent identified according to one of the above-described screening assays. "Treatment", or "treating" as used herein, is defined as the application or administration of a pharmacological agent of the invention to a subject, or application or administration of said agent to an isolated tissue or cell line from a subject, in particular an adult subject, an aging subject or an aged subject such that the desired outcome is achieved. Agents identified according to one of the above-described screening assays can also be useful in the treatment of other disorders, e.g., metabolic disorders, e.g., diabetes, e.g., type II diabetes. Type 2 diabetes is a disease of peripheral insulin resistance combined with pancreatic beta-cell dysfunction. Current evidence indicates that disruption of insulin/insulin-like growth factor (IGF)-1 signaling mechanisms may contribute to defects in both peripheral insulin action and β-cell function. Thus components of the insulin/IGF signaling network and its downstream effector molecules have been identified as attractive therapeutic targets for the rationale treatment of of this disease. Based on the discoveries provided herein, which reveal that defects in neurotransmitter signaling pathways, including the cholinergic, serotonergic and GABA signaling pathways, lead to modulation of lifespan in a mechanism dependent upon the insulin-like signaling pathway molecule DAF-16, components of these neurotransmitter signaling pathways and their downstream effector molecules are attractive therapeutic targets for treatment of type 2 diabetes and other disorders associated with diabetes.

The agent may modulate neurotransmitter signaling by modulating a neurotransmitter signaling pathway molecule selected from, but not limited to, the group consisting of: muscarinic membrane receptor, Gαq, PLCβ, VMAT2, Gαo, DGKθ, Munc13-1, Munc13-2, Munc13-3, PKC, Unc-18, syntaxin, SNAP-25, synaptobrevin, CAPS, RIC-8, diacylglycerol, acetylcholine, γ-aminobutyric acid (GABA), and glutamic acid decarboxylase (GAD). The agent may modulate insulin signaling by modulating an insulin signaling pathway molecule selected from, but not limited to, the group consisting of insulin receptor, insulin-like growth factor, insulin receptor substrate, phosphatidylinositol 3-kinase, PTEN phosphatase, phosphoinositide kinase 1, protein kinase B and forkhead transcription factors.

Such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

The modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

This invention is further illustrated by the following examples which should not be construed as limiting. The contents of all references, patents and published patent applications cited throughout this application are incorporated herein by reference.

EXAMPLES

Materials and Methods used in Examples

Approach. To identify whether additional signaling pathways regulate life span upstream of DAF-2, animals were obtained having a reduction of function mutation in individual genes of neurotransmitter signaling pathways. Mutations in the uncoordinated gene, unc-13, confer extended life span in solitary male worms, while hermaphrodites were reported to have died from internal hatching of larvae (Gems D. & Riddle D. L. (1999) Genetics 154:1597-1610). Unc-13 is implicated in controlling release of neurotransmitters at the neuromuscular junction. In this same study and in a previous report (Ailion et al. 1999 Proc. Natl. Acad. Sci. USA (96) 7394-7397), unc-64 mutant hermaphrodites exhibited extended life span. Unc-64 encodes a homolog of syntaxin, which is part of the SNARE complex that mediates neurotransmitter release by driving membrane fusion of synaptic vesicles. It was postulated that since neuromodulators such as serotonin and acetylcholine have been shown to regulate neurotransmitter release from synaptic vesicles, and given that this regulation involves unc-13, perhaps such neuromodulatory pathways may regulate life span.

This approach was applied to the cholinergic, serotonergic and GABAergic neurotransmitter signaling pathways (for schematic of pathways, see FIG. 1, FIG. 19). First, a panel of C. elegans mutants were produced. C. elegans strains were obtained containing a reduction-of-function mutation in egl-8, cha-1, egl-30, goa-1, dgk-1, unc-13, unc-18, unc-64, unc-25, unc-47, ric-4 and ric-8. C. elegans strains were also constructed containing a reduction-of-function mutation in egl-30, egl-8, unc-13, unc-18, unc-25, unc-47, ric-4 and ric-8 in combination with a loss or reduction-of-function mutation in daf-2 or daf-16. The phenotypes of these mutants were assessed using a standard assay for life span in order to test whether these neurotransmitter signaling pathway genes regulated life span and, further, if they functioned through the insulin signaling pathway defined by daf-2 and daf-16.

Strains and Media. Strains included: N2 (wild type), egl-8 (n488; md1971), cha-1 (p1152), egl-30 (ad805; ad806; n686), goa-1 (n363; n1134; sa734), dgk-1 (nu62; sa748), unc-13 (e450; e1091), unc-18 (e81; e234), daf-2 (e1370), daf-16 (mu86), unc-25 (e156), unc-47 (e307), ric-4 (md1088), ric-8 (md1909), unc-64 (e246), age-1 (hx546). Strains were obtained from the Center of Caenorhabditis elegans Genetics Center (University of Minnesota, Minneapolis, Minn.). Nematodes were cultured under standard conditions (Brenner S. (1974) Genetics 77:71-94).

Strain Construction. To construct double mutant strains, the following general approach was used: daf-2, and daf-16 males were obtained by heat-shock at 30° C. for 6 hours, and these males were used to mate with egl-30, egl-8, unc-13 or unc-18 hermaphrodites. For example, daf-2 (e1370) males were mated to unc-13 hermaphrodites at 15 or 20° C., and 5-7 (15) or 3-4 (20) days later, putative cross progeny were singled to individual plates at 25° C. and allowed to have progeny. Three days later, the plates were scored for the presence of dauers (daf-2). Plates that segregated dauers were kept. Dauers were then returned to 15° C. to recover and singled to individual plates. These recovered dauers were allowed to have progeny and then were tested for presence or absence of the unc-13 mutation by visualization. Matings were done typically at 15° C. and 20° C. depending on the strain.

Strain characterization. The identity of all single and double mutants were confirmed by PCR as well as by phenotypic and complementation analysis. Homozygote F2 worms were identified by dauer formation at 25° C. (daf-2), phenotype (for unc-13, unc-18, goa-1, egl-30, egl-8, unc-25 and unc-47), PCR amplification (daf-16), and body movement coordination (unc-64, ric-4, ric-8). The condition for PCR was 34 cycles of 94° C. for 30 sec, 50° C. for 1 min, and 72° C. for 3 min, followed by 72° C. extension for 10 min. Primers used for PCR of daf-16 were 5'CAATGAGCAATGTGGACAGC-3' (SEQ ID NO: 1) and 5'-CCGTCTGGTCGTTGTCTTTT-3' (SEQ ID NO:2).

Life span assay. Life span assays were performed as described (Apfeld & Kenyon (1998) Cell 95:199-210). Briefly, life span was determined on seeded NGM (nematode growth media) plates at 20° C. Adult hermaphrodites were picked (4-10 per plate) from each strain and allowed to undergo one full generation at 15° C. or 20° C. From these plates, individual L4s or young adults were picked to plates at 20° C. containing 400 µg/ml FUDR. FUDR blocks DNA synthesis and causes animals to lay eggs that do not develop, thereby eliminating the need to transfer animals throughout the life span assay. Survival of the hermaphrodites was measured every few days by tapping. Animals were considered dead if no pharyngeal pumping was evident and they failed to respond to repeated prodding (Johnson T. et al. (1982) PNAS 79:6603-7).

Example 1

Figure 2:
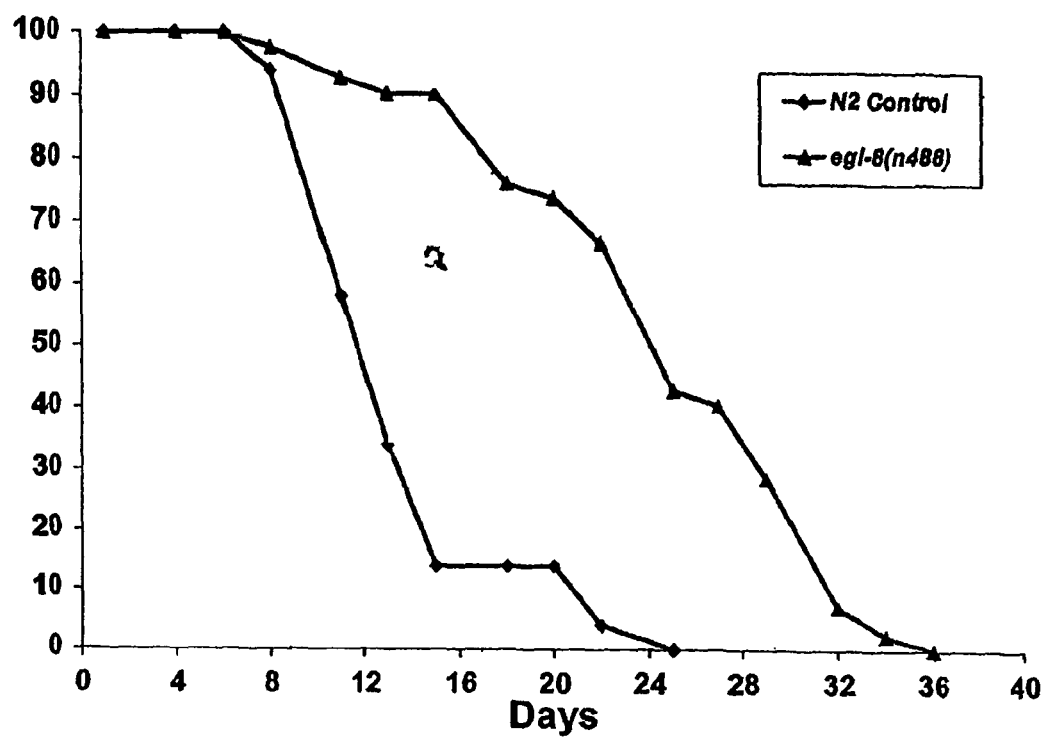
FIG. 2 is a graphical depiction of life span analysis of mutant *C. elegans* strains containing a reduction of function mutation in egl-8.
Figure 3:
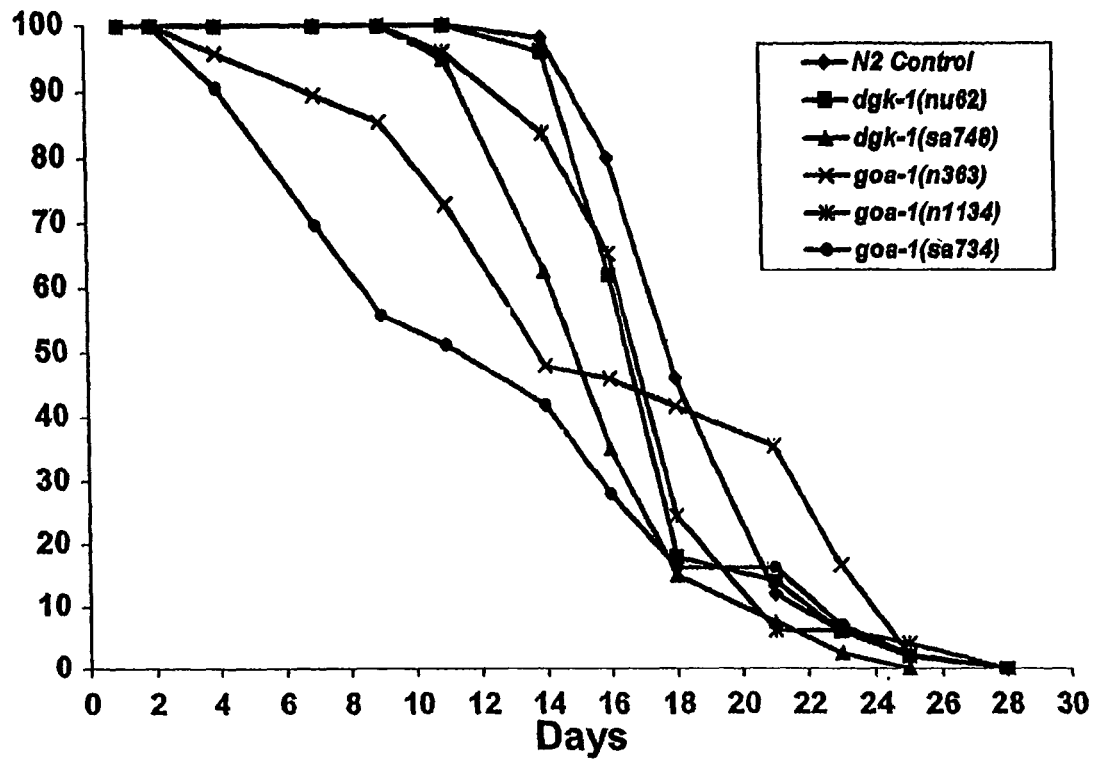
FIG. 3 is a graphical depiction of life span analysis of mutant *C. elegans* strains containing reduction of function mutations in dgk-1 and goa-1.

Reduction of Function Mutations in Genes of the Acetylcholine and Serotonin Neuromodulatory Signaling Pathways Affect Life Span The life span of reduction of function mutants for the acetylcholine neuromodulatory signaling pathway, egl-8, and the serotonin neuromodulatory signaling pathway, goa-1 and dgk-1, were examined to determine if these mutations affected life span when compared to wild type. Results are shown in FIGS. 2 and 3. The egl-8 mutant (n488) significantly extended life span relative to the N2 control strain. The mean life span of the strains were: wild-type=13.8±0.6 (n=50), egl-8 (n488)=25±1.1 (n=42). In contrast, reduction of function mutations in the serotonin pathway genes, including dgk-1 and goa-1, showed statistically significant shorter life spans relative to the N2 control. The mean life span of these strains were: wild-type=19.4±0.4 (n=50), dgk-1 (nu62)= 18.2±0.4 (n=50), dgk-1 (sa748)=16.5±0.5 (n=40), goa-1 (n363)=16.8±1.0 (n=48), goa-1(n1134)=18±0.5 (n=x49, goa-1 (sa734)=13.2±1.0 (n=43). These data are the mean±standard error, (n)=total number of animals tested.).

These results indicate that egl-8 can act as a negative regulator of life span, such that a mutation inactivating the gene causes an extended life span. In contrast, the serotinergic pathway genes dgk-1 and goa-1 act as positive regulators of life span, whereby a mutation that inactivates either gene leads to a shorter life span. These results are consistent with the competing nature of the acetylcholine and serotonin pathways, that of activating and inhibiting, respectively, to regulate release of acetylcholine at synapses.

Example 2

Reduction of Function Mutations in the Uncoordinated Genes unc-13 and unc-18 Confer Life Span Extension An unc-13 (e51) mutant was previously shown to exhibit an extended life span, but only in males that were cultured in single-sex populations (Gems D. & Riddle D. L. (1999) Genetics 154:1597-1610). In this study, unc-13 (e51) hermaphrodites were reported to have died from internal hatching of larvae. In this same study and in a previous report (Ailion et al. 1999 Proc. Natl. Acad. Sci. USA (96) 7394-7397), unc-64 mutant hermaphrodites exhibited extended life span. Unc-64 encodes a homolog of syntaxin, which is part of the SNARE complex that mediates neurotransmitter release by driving membrane fusion of synaptic vesicles. UNC-64/syntaxin interacts with UNC-18, and when so bound is prevented from forming the SNARE complex. It is believed that UNC-13 interacts with UNC-18 to remove UNC-18 from UNC-64/syntaxin and allow UNC-64/syntaxin to form the SNARE complex. All three of these genes are required for normal synaptic transmission in *C. elegans*.

Figure 4:
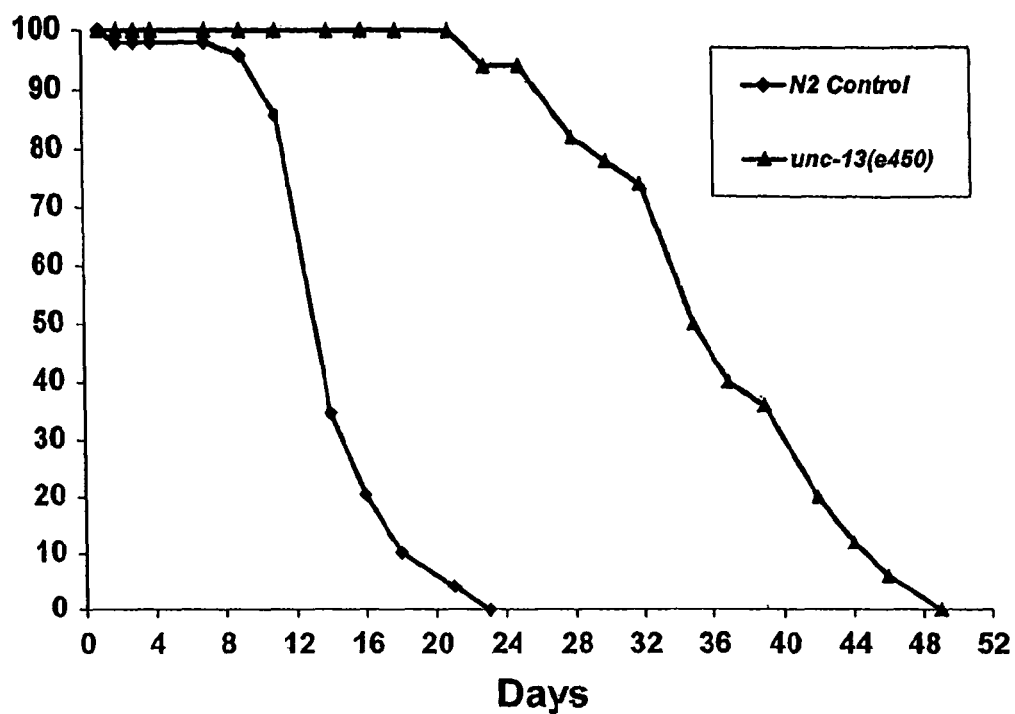
FIG. 4 is a graphical depiction of life span analysis of mutant *C. elegans* strains containing a reduction of function mutation in unc-13.
Figure 5:
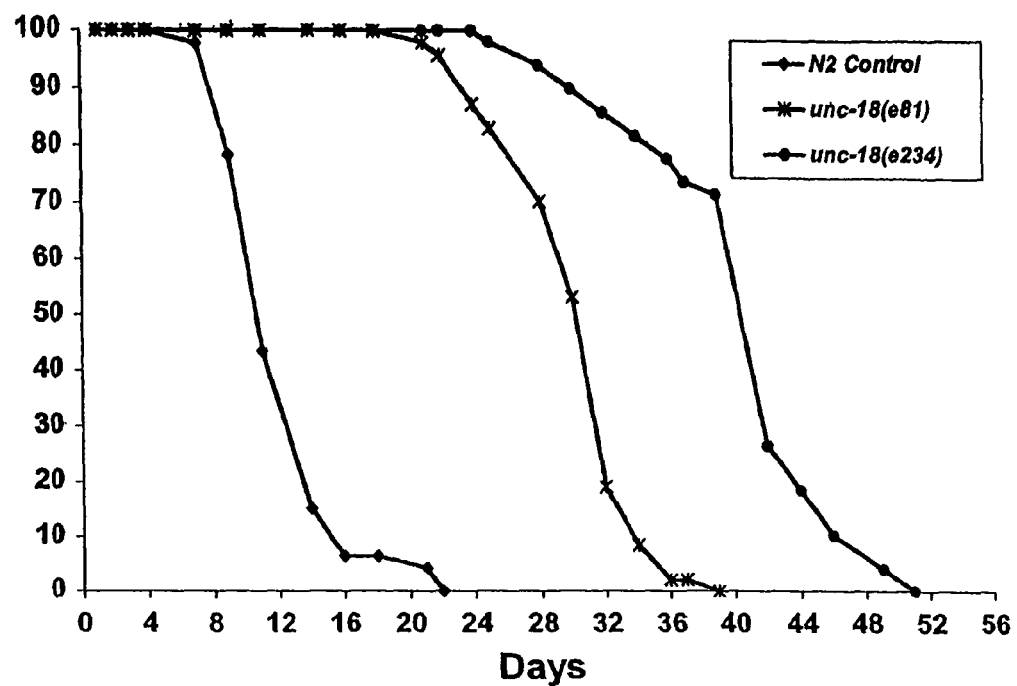
FIG. 5 is a graphical depiction of life span analysis of mutant *C. elegans* strains containing a reduction of function mutation in unc-18.

Reduction of function mutants of the uncoordianted genes unc-13 (e450) and unc-18 (e81 and e234) were examined in life span assays to determine if these mutations affected life span when compared to wild type. Results are shown in FIGS. 4 and 5. The unc-13 mutant (e450) significantly extended hermaphrodite life span relative to the N2 control strain. The mean life span of the strains were: wild-type=14.8±0.5 (n=49), unc-13 (e450)=36.8±1.0 (n=50). Similarly, two distinct reduction of function mutations in unc-18 showed significantly extended life spans relative to the N2 control. The mean life span of these strains were: wild-type=12.5±0.5 (n=46), unc-18 (e81)=30.3±0.6 (n=47), unc-18 (e234)=40.6±0.9 (n=49). These data are the mean±standard error, (n)=total number of animals tested.

In a separate experiment, life spans for additional mutant alleles were as follows: wild-type=14.6±0.6 (n=50), unc-13 (e450)=32.6±0.7 (n=48), unc-13(e1091)=1 8.0±0.4 (n=44), unc-13(e312)=32.3±0.9 (n=44), unc-13(e376)=46.8±0.9 (n=45), unc-13(e51)=28.0±0.8 (n=49), unc-13(n2813)=15.8±0.7 (n=44), unc-13(s69)=41.8±1.0 (n=50)).

These results indicate that both unc-13 and unc-18 acts as a negative regulator of life span in *C. elegans*, such that a mutation inactivating either gene causes an extended life span. These results are consistent with a model in which inhibition of the DAG second-messenger pathway, and thereby decreased acetylcholine release, causes extended life span (FIG. 1). According to this model, the activating role of UNC-13 in acetylcholine release at synapses would predict that reduced function of this gene would lead to a decrease in acetylcholine release and extended life span.

Example 3

Figure 6:
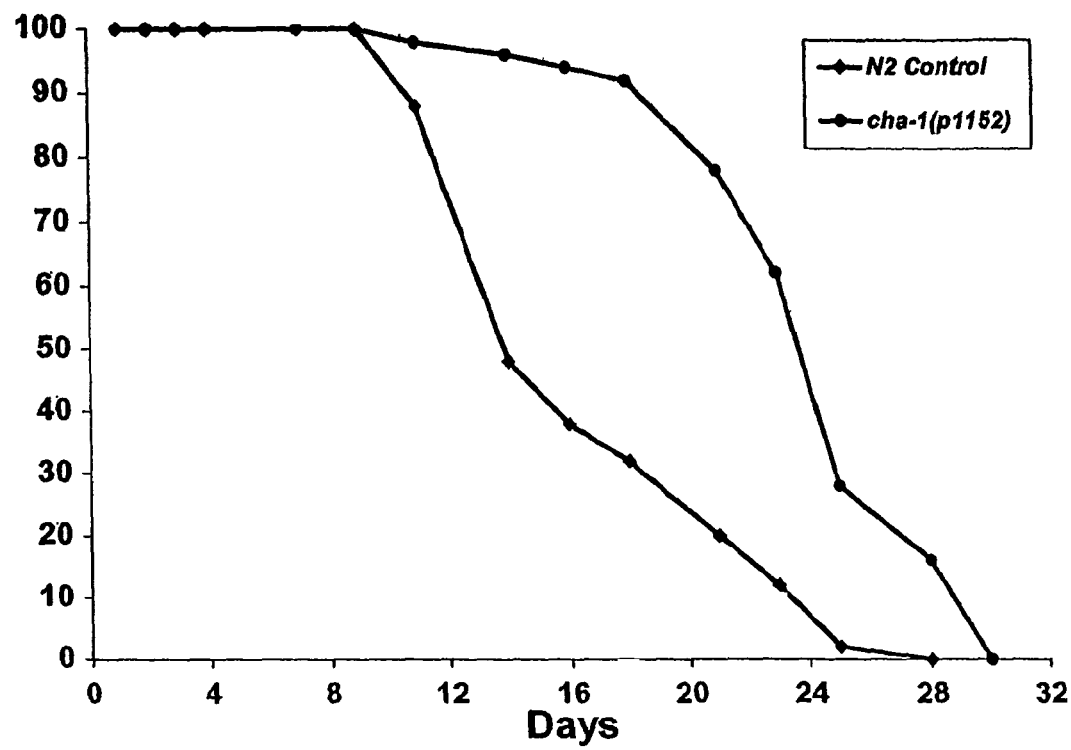
FIG. 6 is a graphical depiction of life span analysis of mutant *C. elegans* strains containing a reduction of function mutation in cha-1.

Reduction of Function Mutations in the Choline Acetyltransferase Gene cha-1 Confers Life Span Extension The structural gene cha-1 encodes for choline acetyltransferase, the enzyme that synthesizes acetylcholine. Reduction of function mutants of the gene cha-1 (p1152) were examined in life span assays to determine if this mutation affected life span when compared to wild type. Results are shown in FIG. 6. The cha-1 mutant extended life span relative to the N2 control strain. The mean life span of the strains were: wild-type=17±0.7, cha-1 (p 1152)=24.5±0.6.

These results indicate that cha-1 acts as a negative regulator of life span in *C. elegans*, such that a mutation inactivating the gene causes an extended life span. This result is consistent with the activating role of cha-1 in the acetylcholine signaling pathway by synthesizing acetylcholine.

In additional life span assays examining mutants for the unc-17 gene, average lifespans were found to be: unc-17 (e245)=28.8±0.5 (n=50), unc-17 (e113)=15.0 ±0.4 (n=50).

Example 4

Combined Reduction of Function Mutations in Uncoordinated Genes (unc-13 or unc-18) and Insulin Signaling Pathway Genes (daf-2 or daf-16) reveal that the Regulation of Life Span Mediated by unc-13 and unc-18 Functions Through the Insulin Signaling Pathway

*C. elegans* strains were constructed harboring reduction of function mutations in unc-13 or unc-18 in combination with a reduction of function mutation in either daf-2 or daf-16. The phenotypes of these mutants were assessed using a standard assay for life span, as described in the Materials and Methods, in order to determine whether these neurotransmitter signaling pathway genes conferred life span extension in a manner dependent or independent of the insulin signaling pathway.

Figure 7:
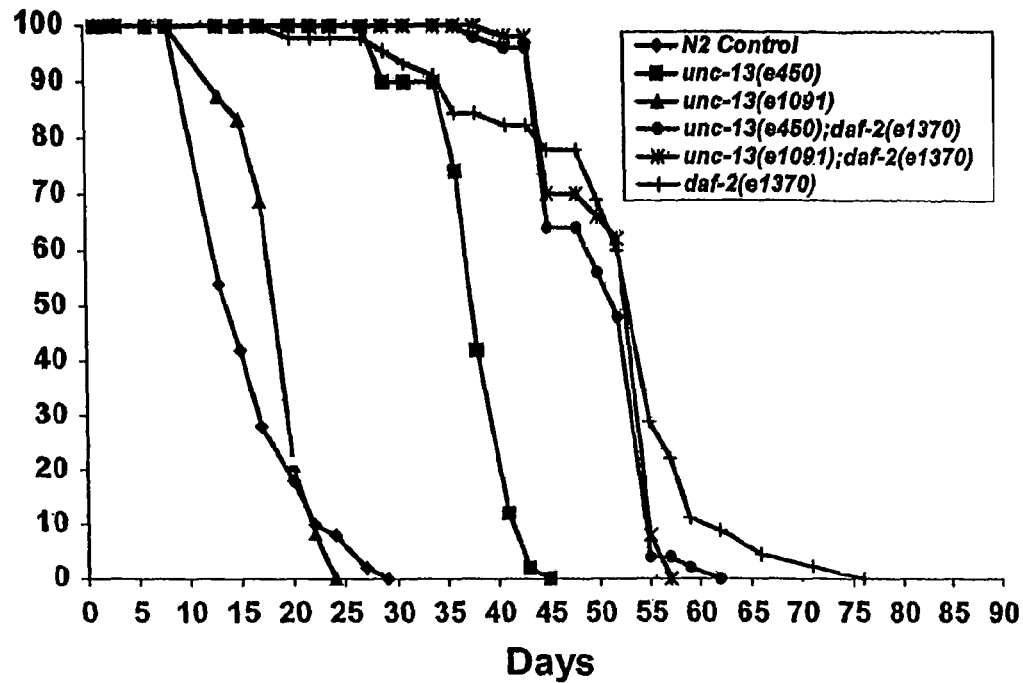
FIG. 7 is a graphical depiction of life span analysis of mutant *C. elegans* strains containing reduction of function mutations in unc-13 and daf-2 alone, and unc-13 in combination with daf-2.

Results of combined reduction of function mutations in unc-13 and daf-2 are shown in FIGS. 7. Two different single reduction of function mutations in unc-13 significantly extended life span relative to an N2 control strain, verifying and extending results depicted in FIG. 4. A single reduction of function mutant for daf-2 also showed a striking increase in life span, as previously described. Combined mutations in unc-13 and daf-2 showed the same life extension as the daf-2 mutation alone. The mean life span of the strains were: wild-type=16.6±0.7 (n=50), unc-13 (e450)=38.3±0.6 (n=50), unc-13 (e1091) 19.1±0.4 days (n=48), daf-2 (e1370)=52±1.6 days (n=45), unc-13 (e450);daf-2 (e1370)=50.8±0.7 days (n=50), unc-13 (e1091); daf-2 (e1370)=51.8±0.7 days (n=50). This result demonstrated that the role of unc-13 in life span extension is dependent upon daf-2, and that unc-13 functions upstream of daf-2 to regulate longevity.

Figure 8:
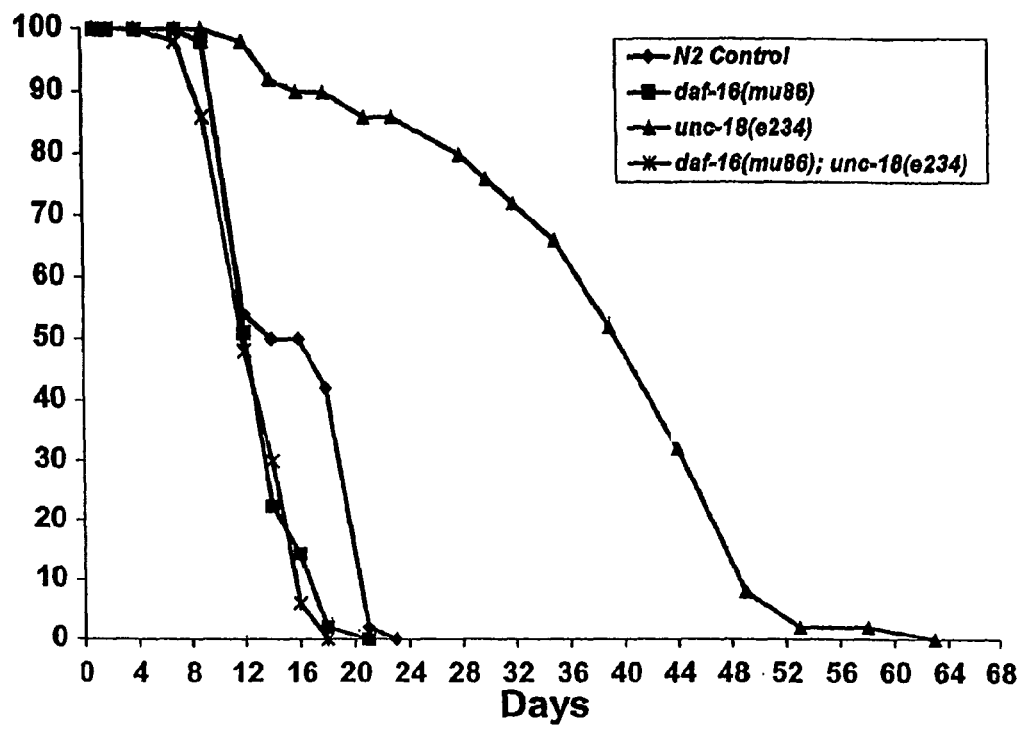
FIG. 8 is a graphical depiction of life span analysis of mutant *C. elegans* strains containing a reduction of function mutation in unc-18, a null mutation in daf-16, and a reduction of function mutation in unc-18 in combination with a null mutation in daf-16.

Results of combined reduction of function mutations in unc-18 and daf-16 are shown in FIG. 8. A single reduction of function mutation in unc-18 significantly extended life span relative to an N2 control strain, verifying results presented in FIG. 5. A single reduction of function mutant for daf-16 showed a slight reduction in life span relative to N2, consistent with previous reports. Importantly, the introduction of a reduction of function mutation in daf-16 into an unc-18 mutant background completely suppressed the life span extension phenotype of unc-18 alone. The mean life span of the strains were: wild-type=16.3±0.6 (n=50), unc-18 (e234)=36.5±1.6 (n=50), daf-16 (mu86)=13.8±0.3 days (n=48), unc-18 (e234);daf-16 (mu86)=13.2±0.4 days (n=49). This result demonstrated that unc-18, like daf-2, absolutely requires daf-16 for its life span regulating effects. Taken together, these results indicated that unc-18 mediates its effect on life span entirely through daf-16 of the insulin-like signaling pathway in *C. elegans*.

Figure 9:
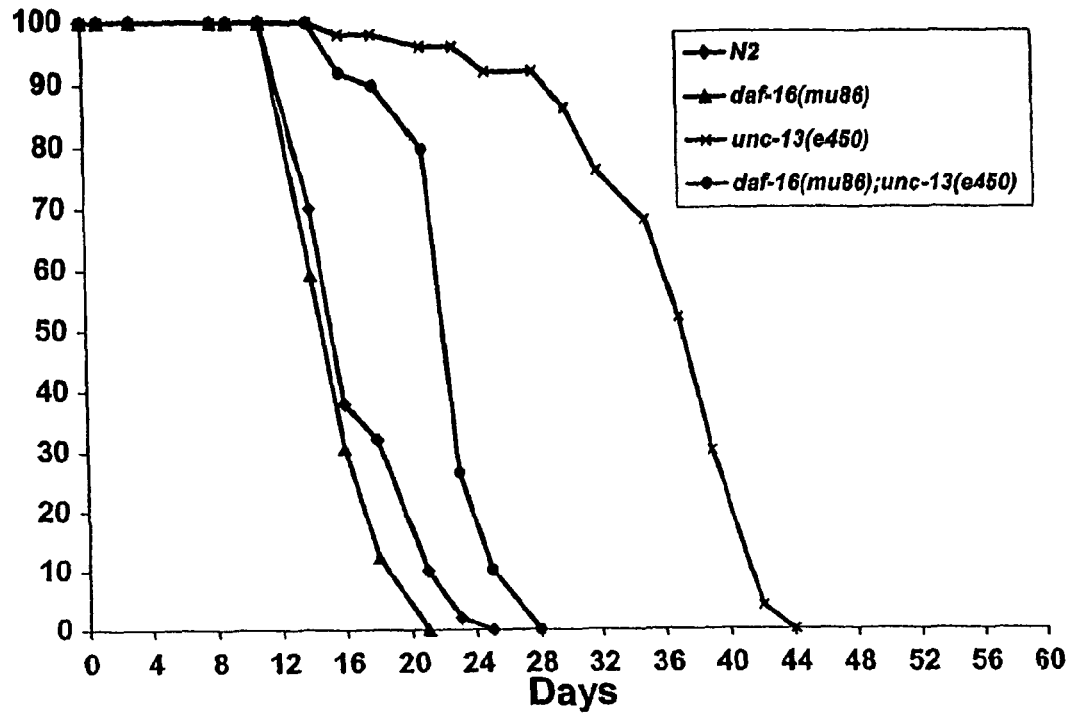
FIG. 9 is a graphical depiction of life span analysis of mutant *C. elegans* strains containing a reduction of function mutation in unc-13, a null mutation in daf-16, and a reduction of function mutation in unc-13 in combination with a null mutation in daf-16.

Results of combined reduction of function mutations in unc-13 and daf-16 are shown in FIG. 9. A single reduction of function mutation in unc-13 significantly extended life span relative to an N2 control strain, verifying results presented in FIG. 4. A single reduction of function mutant for daf-16 showed a slight reduction in life span relative to N2, consistent with previous reports. The introduction of a reduction of function mutation in daf-16 to the unc-13 mutant partially suppressed the life span extension phenotype of unc-13 alone. The mean life span of the strains were: wild-type=17.4±056, unc-13 (e450)=36.7±0.8, daf-16 (mu86)=16.2±0.3 days, unc-13 (e450);daf-16 (mu86)=23±0.4 days. This result demonstrated that unc-13 is partially dependent on daf-16 for its life span regulating effects. These results placed unc-13 acting upstream from daf-16 of the insulin-like signaling pathway in regulating life span in *C. elegans*.

Example 5

Combined Reduction of Function Mutations in Cholinergic Signaling Pathway (egl-30 or egl-8) and Insulin Signaling Pathway (daf-2 or daf-16) Genes Reveal that Regulation of Life Span by the Cholinergic Pathway Functions through the Insulin Signaling Pathway

*C. elegans* strains were constructed harboring reduction of function mutations in egl-30 or egl-8 alone and in combination with a reduction of function mutation in either daf-2 or daf-16. The phenotypes of these mutants were assessed using a standard assay for life span, as described in the Materials and Methods, in order to determine whether these acetylcholine signaling pathway genes conferred the life span extension in a manner dependent or independent of the insulin signaling pathway.

Figure 10:
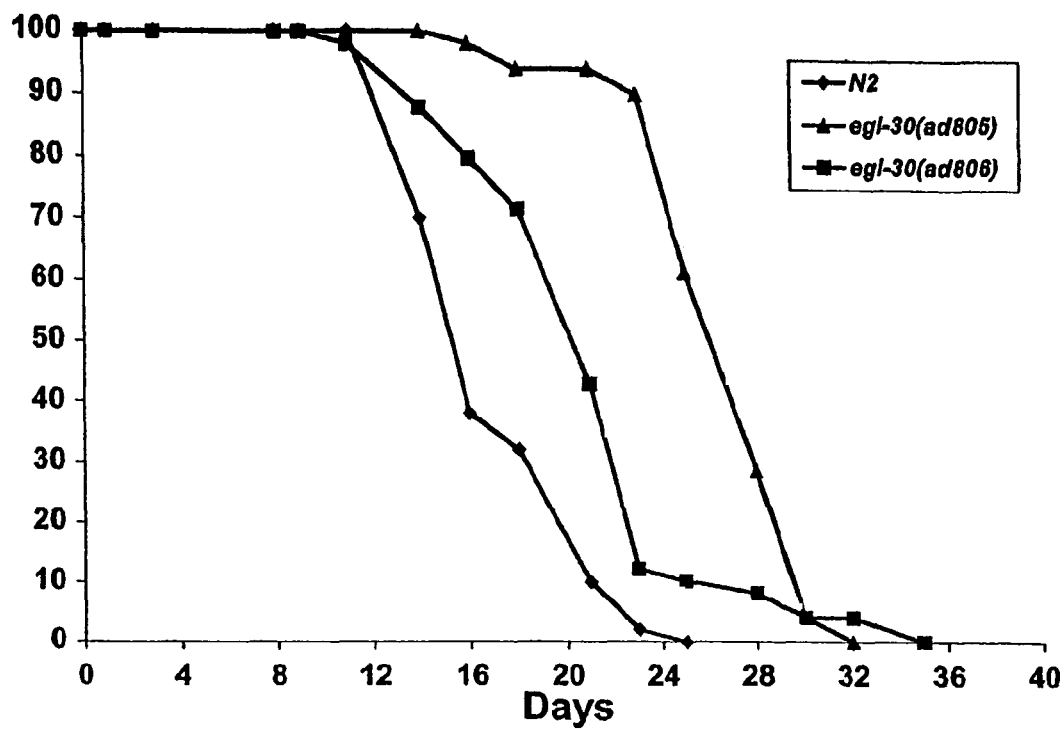
FIG. 10 is a graphical depiction of life span analysis of mutant *C. elegans* strains containing reduction of function mutations in egl-30.
Figure 11:
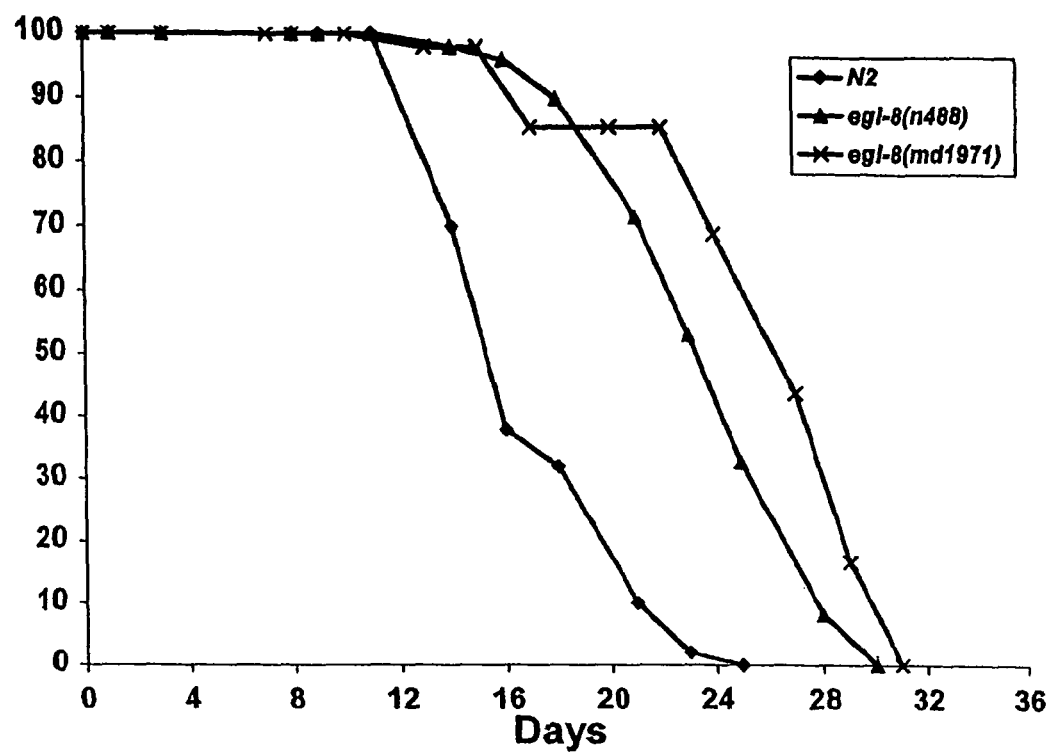
FIG. 11 is a graphical depiction of life span analysis of mutant *C. elegans* strains containing reduction of function mutations in egl-8.

Results of single reduction of function mutants of egl-30 are shown in FIG. 10. The egl-30 mutants (ad805 and ad806) exhibited extended life span relative to the N2 control strain. The mean life span of the strains were: wild-type=17.4±0.5, egl-30 (ad805)=26.9±0.5, egl-30 (ad806)=21.2±0.7. Results of single reduction of function mutants of egl-8 are shown in FIG. 11. The egl-8 mutants (n488 and md1971) exhibited extended life span relative to the N2 control strain, confirming and extending results presented in FIG. 2. The mean life span of the strains were: wild-type=17.4±0.5, egl-8 (n488)= 24.2±0.5, egl-8 (md1971)=26.2±0.7. These results indicate that egl-8 and egl-30, and thus the acetylcholine signaling pathway, act as a negative regulator of life span in *C. elegans*, such that a mutation inactivating genes of this pathway causes an extended life span. This result is consistent with the activating role of EGL-30 and EGL-8 in mediating the release of acetylcholine at synapses.

Figure 12:
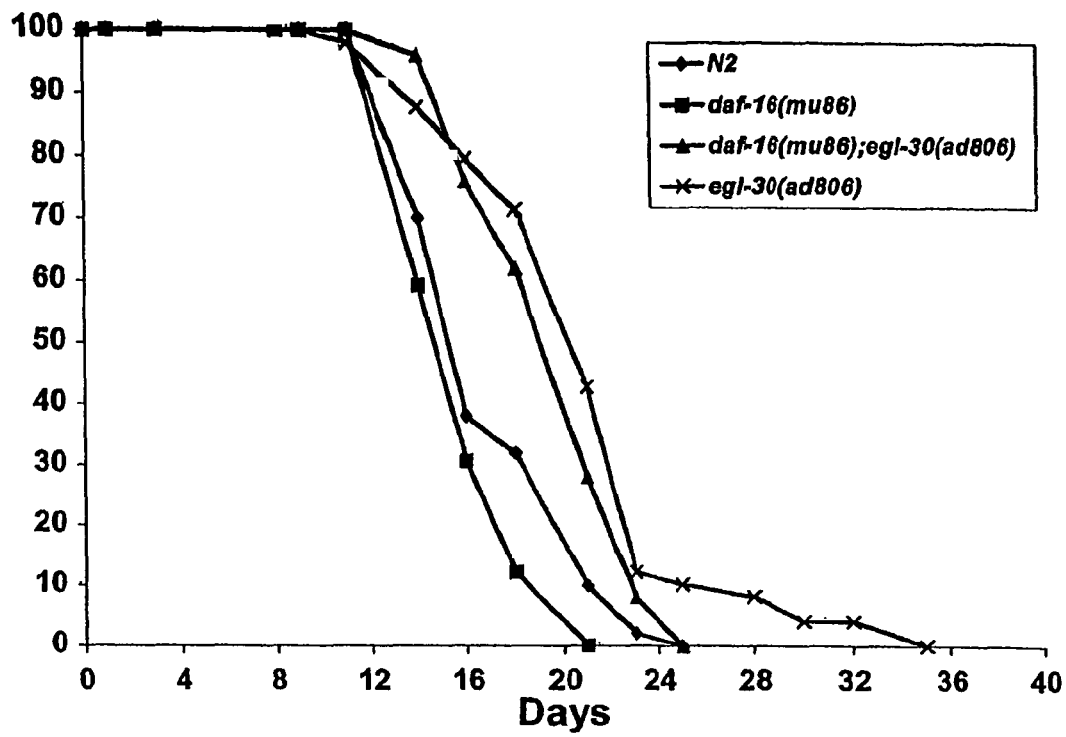
FIG. 12 is a graphical depiction of life span analysis of mutant *C. elegans* strains containing a reduction of function mutation in egl-30, a null mutation in daf-16, and a reduction of function mutation in egl-30 in combination with a null mutation in daf-16.

Results of combined reduction of function mutations in egl-30 and daf-16 are shown in FIG. 12. A single egl-30 mutation extended life span relative to an N2 control strain, as presented in FIG. 11. A single reduction of function mutant for daf-16 showed a slight reduction in life span, as previously described. Introduction of a daf-16 mutation into an egl-30 background slightly suppressed the life span extension phenotype exhibited by the egl-30 single mutant. The mean life span of the strains were: wild-type=17.4±0.5, daf-16 (mu86)= 16.2±0.3, egl-30 (ad806) 21.2±0.7 days , daf-16 (mu86); egl-30 (ad806)=20.0±0.4. This result indicated that the role of egl-30 in life span extension is partially dependent on daf-16.

Figure 13:
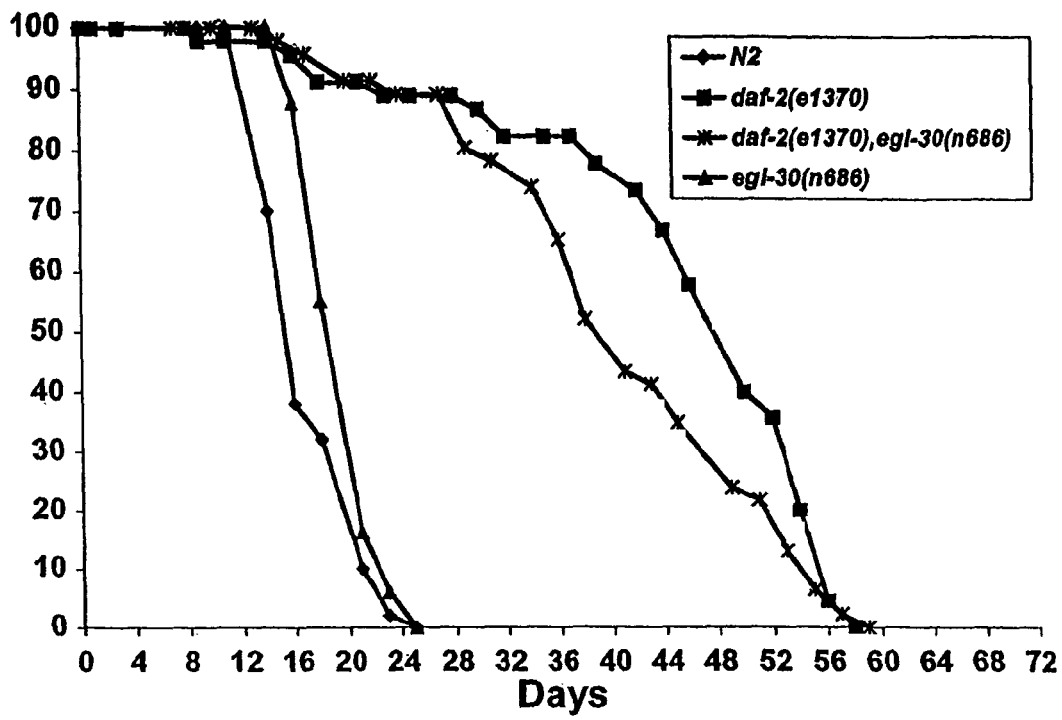
FIG. 13 is a graphical depiction of life span analysis of mutant *C. elegans* strains containing reduction of function mutations in daf-2 and egl-30 alone, and daf-2 in combination with egl-30.

Results of combined reduction of function mutations in egl-30 and daf-2 are shown in FIG. 13. A single reduction of function mutation in egl-30 slightly extended life span relative to an N2 control strain, as presented in FIG. 10. A single reduction of function mutant for daf-2 showed a striking increase in life span, as previously described. Combined mutations in egl-30 and daf-2 showed approximately the same life extension as the daf-2 mutation alone (a slight decrease). The mean life span of the strains were: wild-type=17.4±0.5, egl-30 (n686)=19.9±0.4, daf-2 (e1370)= 45.5±1.9 days, egl-30 (n686);daf-2 (e1370)=40.7±1.7 days. This result indicated that the role of egl-30 in life span extension is dependent upon daf-2, and that egl-30 functions upstream of daf-2 in a linear pathway to regulate longevity.

Figure 14:
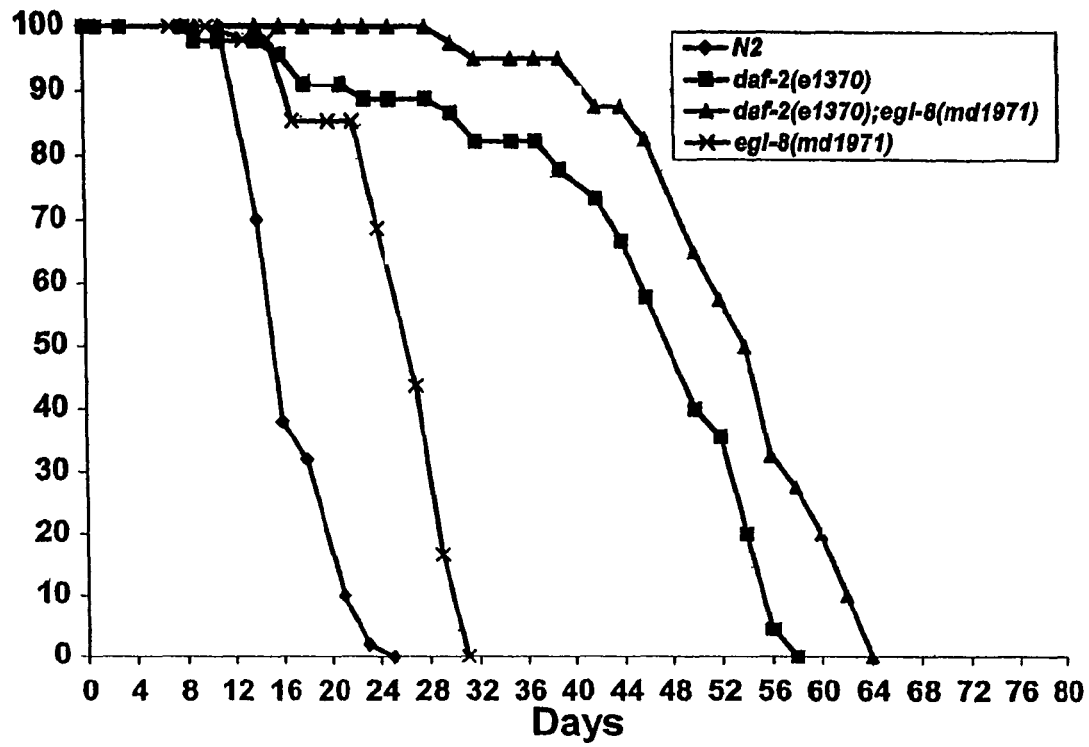
FIG. 14 is a graphical depiction of life span analysis of mutant *C. elegans* strains containing reduction of function mutations in daf-2 and egl-8 alone, and daf-2 in combination with egl-8.

Results of combined reduction of function mutations in egl-8 and daf-2 are shown in FIG. 14. A single reduction of function mutation in egl-8 slightly extended life span relative to an N2 control strain, as presented in FIG. 11. A single reduction of function mutant for daf-2 showed a striking increase in life span, as previously described. Combined mutations in egl-8 and daf-2 showed an enhanced life extension as compared to either mutation alone. The mean life span of the strains were: wild-type=17.4±0.5, egl-8 (md1971)= 26.2±0.7, daf-2 (e1370)=45.5±1.9 days, egl-8 (md1971); daf-2 (e1370)=53.5±1.3 days. This result indicated that egl-8 functions in life span extension in a parallel pathway to that of daf-2.

Example 6

Reduction of Function Mutations in ric-8 Alone, and in Combination with Insulin Signaling Pathway Genes (daf-2 or daf-16), Reveal that ric-8 Regulates Life Span Through a Mechanism Independent of daf-2 but Dependent upon daf-16

In *C. elegans*, ric-8 encodes the protein RIC-8, or synembryn (Miller et.al. 2000 Neuron 27(2) 289-99). RIC-8 encodes a guanine nucleotide exchange factor that is believed to function in conjunction with EGL-30 (Gαq) of the cholinergic neuromodulatory pathway to activate this G protein. The mammalian homolog Ric-8a mediates guanine nucleotide exchange by interacting with GDP-bound Gα proteins and stimulating release of GDP, forming a stable nucleotide-free transition state complex with the Gα protein, and then dissociating on binding of GTP to Gα. *C. elegans* strains harboring single reduction of function mutations in ric-8 were assessed using a standard assay for life span, as described in the Materials and Methods, in order to determine whether this gene also plays a role in regulating life span. In addition, *C. elegans* strains were constructed harboring reduction of function mutations in ric-8 in combination with a reduction of function mutation in either daf-2 or daf-16. The phenotypes of these mutants were assessed in order to determine whether ric-8 affected life span in a manner dependent or independent of the insulin signaling pathway.

Figure 15:
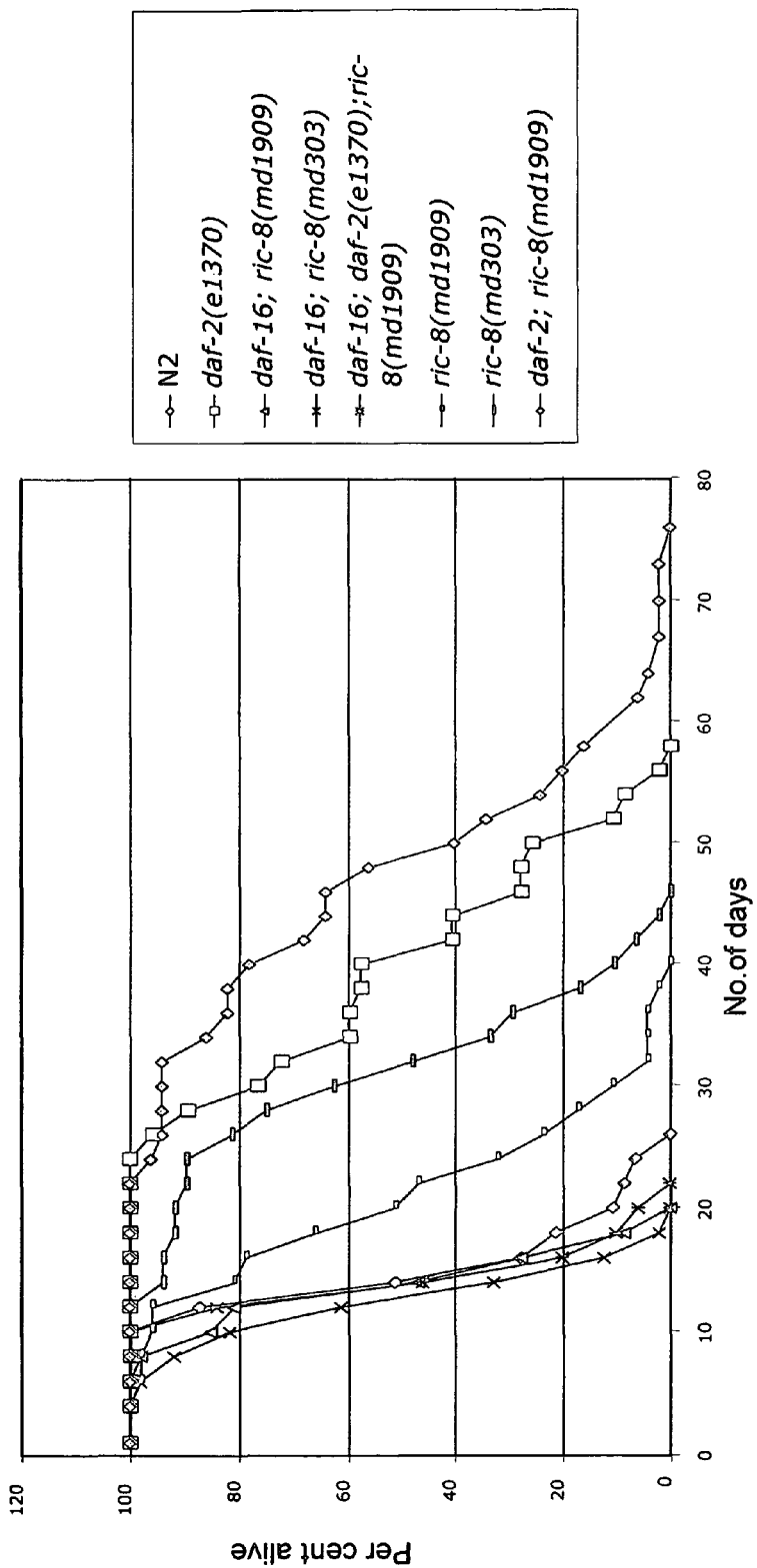
FIG. 15 is a graphical depiction of life span analysis of mutant *C. elegans* strains containing reduction of function mutations in daf-2 and ric-8 alone, reduction of function mutations in ric-8 in combination with a null mutation in daf-16, reduction of function mutations in ric-8 in combination with a reduction of function mutation in daf-2, and a strain containing these same mutations in ric-8 and daf-2 in combination with an additional null mutation in daf-16.

Results of single reduction of function mutants of ric-8 are shown in FIG. 15. Both ric-8 mutants examined (md1909, md303) exhibited extended life span relative to the N2 control strain. The mean life span of the strains were: wild-type=16.2±0.5 (n=47), ric-8 (md1909)=22.2±1.0 (n=47), ric-8 (md303)=32.3±1.1 (n=48). These results indicate that ric-8 acts as a negative regulator of life span in *C. elegans*, such that a mutation inactivating this gene causes an extended life span. This result is consistent with the activating role of RIC-8 on the cholinergic signaling pathway in mediating the release of acetylcholine at synapses.

Results of combined reduction of function mutations in ric-8 and daf-16 or daf-2 are also shown in FIG. 15. Introduction of a daf-6 mutation into a ric-8 background completely suppressed the life span extension phenotype exhibited by the ric-8 single mutants. In contrast, while a single reduction of function daf-2 mutant exhibited an increased life span, as previously described, combined mutations in ric-8 and daf-2 exhibited additive extension of life span as compared to the single mutants alone. Introduction of a third mutation in daf-16 into this double mutant completely suppressed the additive extension of life span down to the life span of the N2 control. The mean life span of the strains were: wild-type=16.2±0.5 (n=47), daf-16 (mu86); ric-8 (md1909) 14.9±0.4 days (n=47), daf-16 (mu86); ric-8 (md303)=13.6±0.4 (n=49), daf-2 (e1370)=41.0±1.4 days (n=47), ric-8 (md1909); daf-2 (e1370)=48.5±1.4 days (n=50), ric-8 (md1909); daf-2 (e1370); daf-16 (mu86)=15.3±0.4 days (n=50). These results indicated that the role of ric-8 in life span extension is completely dependent on daf-16 but independent of daf-2, and suggests that ric-8 functions to regulate life span in a parallel pathway to daf-2 upstream of daf-16.

Example 7

Reduction of Function Mutations in Genes of the GABA Signaling Pathway (unc-25 or unc-47) Alone, and in Combination with Insulin Signaling Pathway Genes (daf-2 or daf-16), Reveal that GABA Signaling Regulates Life Span Through a Mechanism Independent of daf-2 but Dependent Upon daf-16

In *C. elegans*, unc-25 encodes for glutamic acid decarboxylase (GAD), the enzyme that biosynthesizes the classical inhibitory neurotransmitter γ-aminobutyric acid (GABA). Unc-47 encodes a transporter protein that packages GABA into synaptic vesicles. *C. elegans* strains harboring single reduction of function mutations in the GABA signaling pathway genes unc-25 and unc-47 were assessed using a standard assay for life span, as described in the Materials and Methods, in order to determine whether these genes may play a role in regulating life span. In addition, *C. elegans* strains were constructed harboring reduction of function mutations in unc-25 or unc-47 in combination with a reduction of function mutation in either daf-2 or daf-16. The phenotypes of these mutants were assessed in order to determine whether these GABA signaling pathway genes affected life span in a manner dependent or independent of the insulin signaling pathway.

Figure 16:
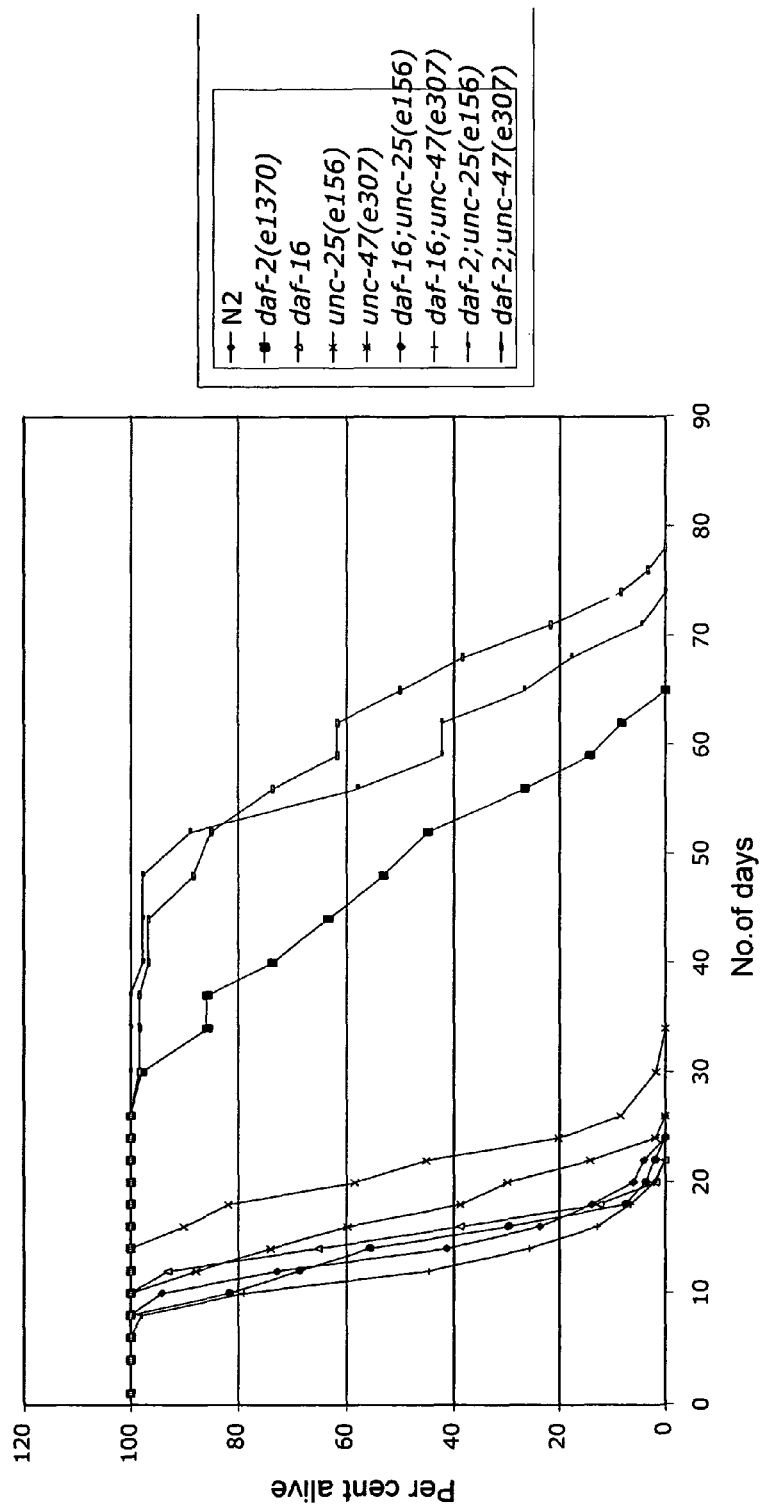
FIG. 16 is a graphical depiction of life span analysis of mutant *C. elegans* strains containing reduction of function mutations in daf-2, unc-25 and unc-47 alone and a null mutation in daf-16 alone, reduction of function mutations in unc-25 or unc-47 in combination with a reduction of function mutation in daf-2, and reduction of function mutations in unc-25 or unc-47 in combination with a null mutation in daf-16.

Results of single reduction of function mutants of unc-25 and unc-47 are shown in FIG. 16. Both the unc-25 mutant (e156) and unc-47 mutant (e307) exhibited extended life span relative to the N2 control strain. The mean life span of the strains were: wild-type=15.1±0.5 (n=51), unc-25 (e156)=22.3±0.5 (n=60), unc-47 (e307)=18.1±0.5 (n=57). These results indicate that unc-25 and unc-47, and thus the GABA signaling pathway, act as a negative regulator of life span in *C. elegans*, such that a mutation inactivating genes of this pathway causes an extended life span.

Results of combined reduction of function mutations in unc-25 or unc-47 and daf-16 are also shown in FIG. 16. A single reduction of function mutant for daf-16 showed a slight reduction in life span, as previously described. Introduction of this daf-16 mutation into an unc-25 or unc-47 background completely suppressed the life span extension phenotype exhibited by the unc-25 and unc-47 single mutants. The mean life span of the strains were: wild-type=15.1±0.5 (n=51), daf-16 (mu86)=16.2±0.3 (n=57), daf-16 (mu86); unc-25 (e156) 15.0±0.5 days (n=54), daf-16 (mu86); unc-47 (e307)=13.4±0.4 (n=47). This result indicated that the role of unc-25 and unc-47 in life span extension is completely dependent on daf-16.

Results of combined reduction of function mutations in unc-25 or unc-47 and daf-2 are also shown in FIG. 16. A single reduction of function mutant for daf-2 showed a striking increase in life span, as previously described. Combined mutations in unc-25 or unc-47 and daf-2 exhibited additive extension of life span as compared to the single mutants alone. The mean life span of the strains were: wild-type=15.1±0.5 (n=51), daf-2 (e1370)=50.0±1.4 days (n=49), unc-25 (e156); daf-2 (e1370)=61.0±0.6 days (n=45), unc-47 (e307); daf-2 (e1370)=63.9±1.3 days (n=60). This result indicated that the role of unc-25 and unc-47 in life span extension is independent of daf-2, and suggests that GABA signaling functions to regulate life span in a parallel pathway to daf-2 upstream of daf-16.

Example 8

Reduction of Function Mutations in unc-25 of the GABA Signaling Pathway in Combination with Reduction of Function Mutation in egl-30 of the Cholinergic Signaling Pathway Reveal that egl-30 Regulates Life Span Through a Mechanism Partially Dependent Upon unc-25

Figure 17:
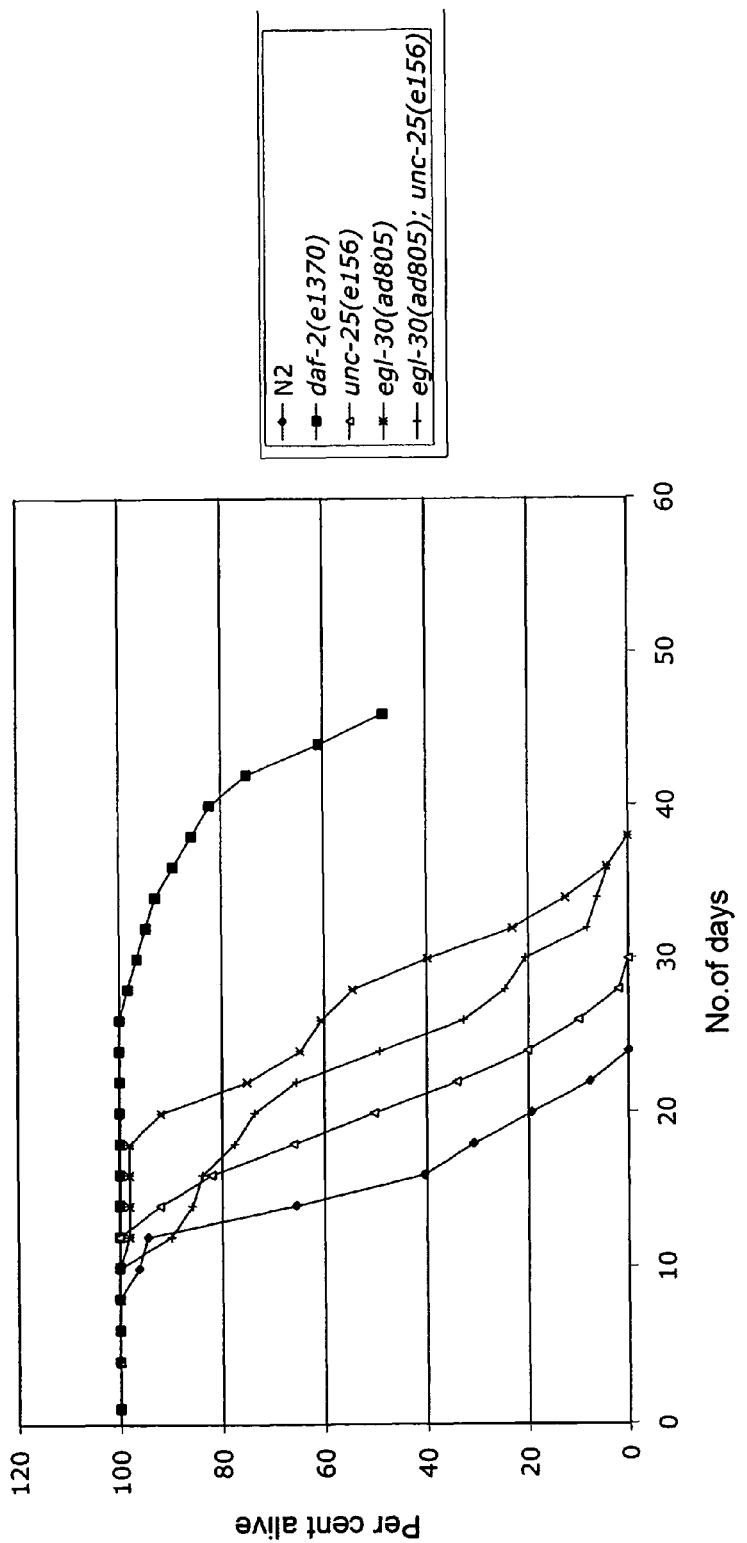
FIG. 17 is a graphical depiction of life span analysis of mutant *C. elegans* strains containing reduction of function mutations in daf-2, unc-25 and egl-30 alone, and a reduction of function mutation in unc-25 in combination with a reduction of function mutation in egl-30.

A *C. elegans* strain was constructed harboring a reduction of function mutation in unc-25 in combination with a reduction of function mutation in egl-30. The phenotypes of the single and double mutants were assessed in a lifespan assay. Results of single reduction of function mutants of unc-25 and egl-30 and the double mutant for unc-25 and egl-30 are shown in FIG. 17. Both the unc-25 mutant (e156) and egl-30 mutant (ad805) exhibited extended life span relative to the N2 control strain, while the double mutant exhibited an intermediate life span between the two single mutants. The mean life span of the strains were: wild-type=17.1±0.5 (n=24), unc-25 (e156)=22.1±0.6 (n=30), egl-30 (ad805)=28.3±0.8 (n=38), unc-25 (e156); egl-30 (ad805)=24.4±1.0 (n=38). These results indicate that egl-30 regulates life span through a mechanism partially dependent upon unc-25.

Example 9

Reduction of Function Mutations in ric-4 Alone, and in Combination with Insulin Signaling Pathway Genes (daf-2 or daf-16), Reveal that ric-4 can Regulate Life Span Through a Mechanism Dependent Upon daf-16

The gene ric-4 in *C. elegans* encodes SNAP-25, a component of the core synaptic vesicle fusion machinery, and is required for SNARE complex multimerization (J. E. Richmond and K. S. Broadie (2002) *Curr. Opin. Neurobiology* 12:499-507). Defects in ric-4 inhibit cholinergic transmission (ibid). *C. elegans* strains harboring single reduction of function mutations in ric-4 were assessed using a standard assay for life span, as described in the Materials and Methods, in order to determine whether these genes may play a role in regulating life span. In addition, *C. elegans* strains were constructed harboring reduction of function mutations in ric-4 in combination with a reduction of function mutation in either daf-2 or daf-16. The phenotypes of these mutants were assessed in order to determine whether ric-4 affected life span in a manner dependent or independent of the insulin signaling pathway.

Figure 18:
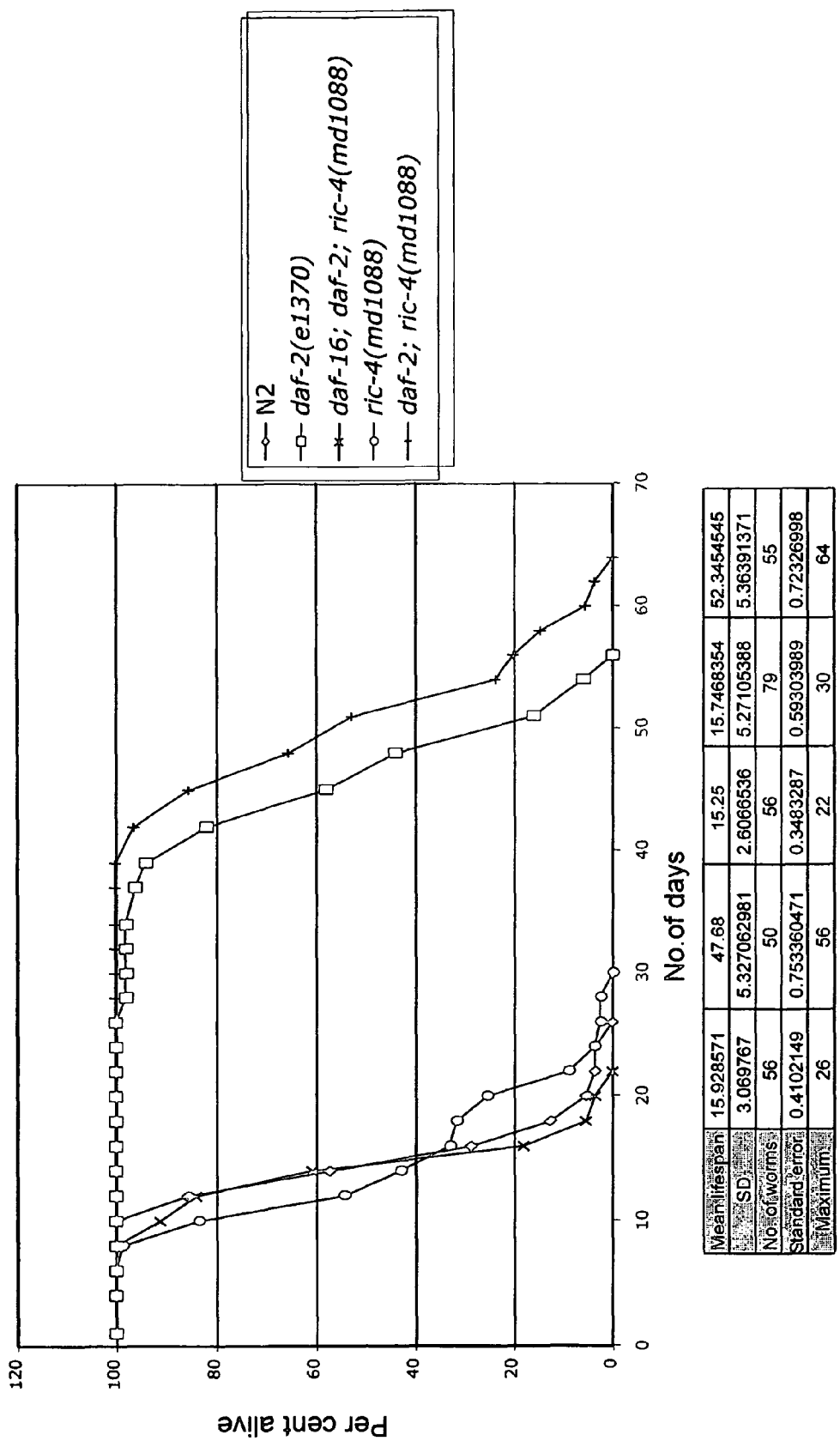
FIG. 18 is a graphical depiction of life span analysis of mutant *C. elegans* strains containing reduction of function mutations in daf-2 and ric-4 alone, reduction of function mutations in ric-4 in combination with a reduction of function mutation in daf-2, and a strain containing these same mutations in ric-4 and daf-2 in combination with an additional null mutation in daf-16.

Results of single reduction of function mutant ric-4 and combined reduction of function mutations in ric-4 and daf-2 and/or daf-16 are shown in FIG. 18. The ric-4 mutant (md1088) exhibited no effect on life span relative to the N2 control strain. However, while a single reduction of function daf-2 mutant exhibited an increased life span, as previously described, combined mutations in ric-4 and daf-2 exhibited a synergistic effect for extension of life span as compared to the single mutants alone. Introduction of a third mutation in daf-16 into this double mutant completely suppressed the extension of life span such that it was similar to the life span of the N2 control. The mean life span of the strains were: wild-type=15.9±0.4 (n=56), ric-4 (md1088)=15.7±0.6 (n=79), daf-2 (e1370)=47.7±0.8 days (n=50), ric-4 (md1088); daf-2 (e1370)=52.3±0.7 days (n=55), ric-4 (md1088); daf-2 (e1370); daf-16 (mu86)=15.3±0.4 days (n=56).

These results indicated that the role of ric-4 in life span extension is completely dependent on daf-16 but independent of daf-2, and suggests that ric-4 functions to regulate life span in a parallel pathway or upstream to daf-2, and functions upstream of daf-16. These results indicate that ric-4 acts as a negative regulator of life span in *C. elegans*, such that a mutation inactivating this gene in a defective daf-2 background causes an extended life span. This result is consistent with the activating role of RIC-4 in mediating the release of acetylcholine at synapses.

Summary of Examples 6-9

Results of lifespan analysis set forth in Examples 6-8 is summarized in the following Table:

| Double/triple mutants | Lifespan extension relative to single mutant |
| --- | --- |
| daf-2; ric-8 | > daf-2 |
| daf-16; ric-8 | = daf-16 |
| daf-16; daf-2; ric-8 | = daf-16 |
| daf-2; ric-4 | > daf-2 |
| daf-16; daf-2; ric-4 | = daf-16 |
| daf-2; unc-25 | > daf-2 |
| daf-2; unc-47 | > daf-2 |
| daf-16; unc-25 | = daf-16 |
| daf-16; unc-47 | = daf-16 |
| egl-30; unc-25 | > unc-25, < egl-30 |

Example 10

Evaluation of Stress Resistance and Body Movement Coordination in Mutants of Genes in Neurotransmitter Signaling Pathways Reduction of function mutations in jnk-1, jkk-1 and mek-1 result in defects in coordinated body movements and/or resistance to stress, such as heavy metals (Villanueva A. et al. (2001) *EMBO J* 20:5114-5128; Koga M. et al. (2000) *EMBO J* 19:5148-5156; Kawasaki M. et al. (1999) *EMBO J* 18:3604-3615). These defects in coordination are primarily due to the fact that at least jnk-1 and jkk-1 are expressed in both the cell bodies and the axons of most neurons.

In order to evaluate resistance to various stresses, including UV, oxidative and heat stress, as well as body movement coordination, *C. elegans* strains harboring a reduction of function mutation in either the cholinergic or serotonergic signaling pathways, either alone or in combination with a reduction of function mutation in the insulin signaling pathway genes daf-2 or daf-16 are generated as described in the Materials and Methods. Mutants are then examined for stress resistance and the movement phenotype as follows:

UV stress. 30-40 L4~young adult animals are removed from a seeded plate, washed in 1XS-Basal, then transferred to an unseeded NGM plate. Animals are exposed to 40 J/m2 in a Stratalinker 2400 (Stratagene). Animals are removed from the unseeded plate and placed on a seeded one. Life span is calculated from the day of UV treatment. UV treatment often leads to egg laying defects and bagged adults. These animals are censored from life span calculations.

Oxidative stress. For each strain to be tested, 100 L1 animals are placed to develop to adulthood on NGM plates containing different concentrations of paraquat (0 mM, 0.2 mM, 0.4 mM, 0.6 mM, and 0.8 mM) (Feng et al. (2001) Dev. Cell. 1:1-20). For each strain, worms are monitored each day until 6 days after the first worms become adults. The percentage of worms that reach adulthood is expressed as survival.

Heat stress. Intrinsic thermotolerance is measured as a percent of a cohort of L4~young adult worms that survive a near-lethal heat shock. Specifically, 30-40 wild type or mutant adults are placed on a seeded NGM plate and left to lay eggs for 3-4 hours. Adults are removed and eggs are allowed to develop until 3 days past L4 molt. Next, 30-40 rolling adults are placed on a small seeded NGM plate at 35° C. for 24 hours. The worms are then scored for viability.

Body movement coordination assay: Single L4~young adult worm is placed on a seeded NGM plate and body bending per minute is recorded by manual counting under the microscope. The locomotion of worms is observed after 1 min, 10 min, and 60 min by drawing the line on the plate lid along the tracks made by worms.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

1. Villanueva, A., Lozano, J., Morales, A., Lin, X., Deng, X., Hengartner, M. O. & Kolesnick, R. N.jkk-1 and mek-1 regulate body movement coordination and response to heavy metals through jnk-1 in *Caenorhabditis elegans*. *EMBO J* 20, 5114-5128 (2001).
2. Morris, J. Z., Tissenbaum, H. A. & Ruvkun, G. A phosphatidylinositol-3-OH kinase family member regulating longevity and diapause in *Caenorhabditis elegans*. *Nature* 382, 536-539 (1996).
3. Kimura, K., Tissenbaum, H. A., Liu, Y. & Ruvkun, G. The daf-2 insulin receptor family member regulates longevity and diapause in *Caenorhabditis elegans*. *Science* 277, 942-946 (1997).
4. Ogg, S., Paradis, S., Gottlieb, S., Patterson, G. I., Lee, L., Tissenbaum, H. A. & Ruvkun, G. The Fork head transcription factor DAF-16 transduces insulin-like metabolic and longevity signals in *C. elegans*. *Nature* 389, 994-9 (1997).
5. Tissenbaum, H. A. & Ruvkun, G. An insulin-like signaling pathway affects both longevity and reproduction in *Caenorhabditis elegans*. *Genetics* 148, 703-717 (1998).
6. Cassada, R. C. & Russell, R. The dauer larva, a post-embryonic developmental variant of the nematode *Caenorhabditis elegans*. *Developmental Biology* 46, 326-342 (1975).
7. Klass, M. R. & Hirsh, D. I. Nonaging developmental variant of *C. elegans*. *Nature* 260, 523-525 (1976).

8. Riddle, D. L. & Albert, P. S. in *C. elegans II* (eds. Riddle, D. L., Blumenthal, T., Meyer, B. J. & Priess, J R.) 739-768 (Cold Spring Harbor Laboratory Press, 1997).
9. Pierce, S. B., Costa, M., Wisotzkey, R., Devadhar, S., Homburger, S. A., Buchman, A. R., Ferguson, K. C., Heller, J., Platt, D. M., Pasquinelli, A. A., Liu, L. X., Doberstein, S. K. & Ruvkun, G. Regulation of DAF-2 receptor signaling by human insulin and ins-1, a member of the unusually large and diverse *C. elegans* insulin gene family. *Genes and Development* 15, 672-686 (2001).
10. Gregoire, F. M., Chomiki, N., Kachinskas, D. & Warden, C. H. Cloning and developmental regulation of a novel member of the insulin-like family in *Caenorhabditis elegans*. *Biochem Biophys Res Commun* 249 385-390 (1998).
11. Kido, Y., Nakae, J. & Accili, D. The Insulin receptor and its cellular targets. *Journal of Clinical Endocrinology and Metabolism* 86, 972-979 (2001).
12. Alessi, D. R. & Downes, C. P. The role of PI 3-kinase in insulin action. *Biochim Biophys Acta* 1436 151-164 (1998).
13. Lithgow, G. J., White, T. M., Hinerfeld, D. A. & Johnson, T. E. Thermotolerance of a long-lived mutant of *Caenorhabditis elegans*. *J. Gerontol.* 49, B270-276 (1994).
14. Lithgow, G. J., White, T. M., Melov, S. & Johnson, T. E. Thermotolerance and extended life-span conferred by single-gene mutations and induced by thermal stress. *Proc NatlAcadSci USA* 92, 7540-4 (1995).
15. Murakami, S. & Johnson, T. E. A genetic pathway conferring life extension and resistance to UV stress in *Caenorhabditis elegans*. *Genetics* 143, 1207-1218 (1996).
16. Honda, Y. & Honda, S. The daf-2 gene network for longevity regulates oxidative stress resistance and Mn-superoxide dismutase gene expression in *Caenorhabditis elegans*. *FASED J* 13, 1385-1393 (1999).
17. Baryste, D., Lovejoy, D. A. & Lithgow, G. J. Longevity and heavy metal resistance in daf-2 and age-1 long-lived mutants of *Caenorhabditis elegans*. *FasEB J* 15, 627-634 (2001).
18. Friedman, D. B. & Johnson, T. E. A mutation in thcage-1 gene in *Caenorhabditis elegans* lengthens life and reduces hermaphrodite fertility. *Genetics* 118, 75-86 (1988).
19. Klass, M. R. A method for the isolation of longevity mutants in the nematode *Caenorhabditis elegans* and initial results. *Mechanisms of Ageing and Dev.* 22, 279-286 (1983).
20. Paradis, S. & Ruvkun, G. *Caenorhabditis elegans* Akt/PKB transduces insulin receptor-like signals from AGE-1 PI3 kinase to the DAF-16 transcription factor. *Genes and Development* 12, 2488-2498 (1998).
21. Paradis, S., Ailion, M., Toker, A., Thomas, J. H. & Ruvkun, G. A PDK1 homolog is necessary and sufficient to transduce AGE-1 PI3 kinase signals that regulate diapause in *Caenorhabditis elegans*. *Genes Dev* 13, 1438-1452 (1999).
22. Rouault, J. P., Kuwabara, P. E., Sinilnikova, O. M., Duret, L., Thierry-Mieg, D. & Billaud, M. Regulation of dauer larva development in Caenorhabditis elegans by daf-18, a homologue of the tumour suppressor PTEN. *Current Biology* 9, 329-332 (1999).
23. Ogg, S. & Ruvkun, G. The *C. elegans* PTEN homolog, DAF-18, acts in the insulin receptor-Like metabolic signaling pathway. *Molecular Cell* 2, 887-893 (1998).
24. Mihaylova, V. T., Borland, C. Z., Manjarrez, L., Stem, M. J. & Sun, H. The PTEN tumor suppressor homolog in *Caenorhabditis elegans* regulates longevity and dauer formation in an insulin receptor-Like signaling pathway. *Proc Natl Acad Sci USA* 96, 7427-7432 (1999).
25. Gil, E. B., Malone Link, E., Liu, L. X., Johnson, C. D. & Lees, J. A. Regulation of the insulin-Like developmental pathway of *Caenorhabditis elegans* by a homolog of the PTEN tumor suppressor gene. *Proc Natl Acad Sci USA* 96, 2925-2930 (1999).
26. Maehama, T. & Dixon, J. E. The tumor suppressor, PTEN/MMAC1, dephosphorylates the lipid second messenger, phosphatidylinositol 3,4,5-trisphosphate. *Journal of Biological Chemistry* 273, 13375-13378 (1998).
27. Lin, K., Dorman, J. B., Rodan, A. & Kenyon, C. daf-16: An HNF-3/forkhead family member that can function to double the life-span of *Caenorhabditis elegans*. *Science* 278, 1319-1322 (1997).
28. Kenyon, C. in *C. elegans II* (eds. Riddle, D. L., Blumenthal, T., Meyer, B. J. & Priess, J. R.) 791-813 (Cold Spring Harbor Lab. Press, Plainview, N.Y., 1997).
29. Gems, D., Sutton, A. J., Sundermeyer, M. L., Albert, P. S., King, K. V., Edgley, M. L., Larsen, P. L. & Riddle, D. L. Two pleiotropic classes of daf-2 mutation affect larval arrest, adult behavior, reproduction and longevity in *Caenorhabditis elegans*. *Genetics* 150, 129-155 (1998).
30. Sone, H., Suzuki, H., Takahashi, A. & N., Y. Disease model: hyperinsulinemia and insulin resistance. Part A-targeted disruption of insulin signaling or glucose transport. *Trends in Molecular Medicine* 7, 320-322 (2001).
31. Ip, T. Y. & Davis, R. J. Signal transduction by the c-Jun N-terminal kinase (JNK)- from inflammation to development. *Current Opinion in Cell Biology* 10, 205-219 (1998).
32. Weston, C. R. & Davis, R. J. The JNK signal tranduction pathway. *Current Opinion in Genetics and Development* 12, 14-21 (2002).
33. Aguirre, V., Uchida, T., Yenush, L,., Davis, R. & White, M. F. The c-Jun $NH_2$-ierminal kinase promotes insulin resistance during association with insulin receptor substrate-1 and phosphorylation of $Ser^{307}$. *Journal of Biological Chemistry* 275, 9047-9054 (2000).
34. Koga, M., Zwaal, R., Guan, K.-L., Avery, L. & Ohshima, Y. A *Caenorhabditis elegans* MAP kinase kinase, MEK-1, is involved in stress responses. *EMBO J* 19, 5148-5156 (2000).
35. Kawasaki, M., Hisamoto, N., Iino, Y., Yamamoto, M., Ninomiya-Tsuji, J. & Matsumoto, K. A *Caenorhabditis elegans* INK signal transduction pathway regulates coordinated movement via type-D GABAergic motor neurons. *EMBO J* 18, 3604-3615 (1999).
36. Tissenbaum, H. A. & Guarente, L. Model systems as a guide to mammalian aging. *Developmental Cell* 2 9-19 (2002).
37. Byrd, D. T., Kawasaki, M., Walcoff, M., Hisamoto, N., Matsumoto, K. & Jin, Y. UNC-16, a JNK-signaling scaffold protein regulates vesicle transport in *C. elegans*. *Neuron* 32, 787-800 (2001).
38. Yasuda, J., Whitmarsh, A. J., Cavanaugh, J., Sharma, M. & Davis, R. J. The IIP group od mitogen-activated protein kinase scaffold proteins. *Molecular and Cellular Biology* 19, 7245-7254 (1999).
39. Dlakic, M. A new family of putative insulin receptor-like proteins in *C. elegans*. Current Biology (2002) 12(5) R155-R157.
40. Wokow C. A., Munoz M. J., Riddle D. L. & Ruvkun G. Insulin receptor substrate and p55 orthologous adaptor proteins function in the *Caenorhabditis elegans* daf-1/Insulin-like signaling pathway (2002) J. Biol. Chem. 277 (51): 49591-49597.

41. Apfeld J. & Kenyon C., Cell nonautonomy of *C. elegans* daf-2 function in the regulation of diapause and life span (1998) Cell 95: 199-210
42. Feng J., Bussiere F., Hekimi S. Mitochondrial electron transport is a key determinant of life span in *Caenorhabditis elegans*. 2001 Cell 1:1-20.
43. Holzenberger M. Dupont J., Ducos B., Leneuve P., Geloen A., Even P. C., Cervera P., Le Bouc Y., IGF-1 receptor regulates lifespan and resistance to oxidative stress in mice. (2002) Nature, Dec. 4, in press.
44. Jia K., Albert P. S. and Riddle, D. L., DAF-9, a cytochrome P450 regulating *C. elegans* larval development and adult longevity. (2002) Development 129:221-231.
45. Gerisch B., Weitzel C., Kober-Eisermann C., Rottiers V. and Antebi A. A hormonal signaling pathway influencing *C. elegans* metabolism, reproductive development, and life span. (2001) Dev. Cell., 1(6):841-51.

What is claimed:

1. A method for identifying an agent capable of extending the mature life phase of a nematode, comprising:
   contacting a nematode having altered activity or expression of a cholinergic pathway molecule selected from the group consisting of EGL-8, RIC-8 and RIC-4, and altered activity or expression of DAF-2 with a test agent, wherein said altered activity or expression of the cholinergic pathway molecule or said altered activity or expression said DAF-2 extends the mature life phase of the nematode;
   assaying for the ability of the test agent to increase the lifespan of the nematode as compared to a suitable control, and
   selecting an agent that increases the lifespan,
   to thereby identify an agent capable of extending the mature life phase of a nematode.

2. A method for identifying an agent capable of extending the mature life phase of a nematode, comprising:
   contacting nematode with a test agent, said nematode having a cholinergic pathway;
   assaying for the ability of the test agent to inhibit the one or more of the expression, intracellular level, extracellular level, activity, post-translational modification, interaction or cellular localization of an indicator of said cholinergic pathway as compared to a suitable control, wherein the indicator of said cholinergic pathway is selected from the group consisting of EGL-8, RIC-8-and RIC-4; and
   selecting an agent that inhibits the cholinergic pathway;
   to thereby identify an agent capable of extending the mature life phase of a nematode.

3. A method for identifying an agent capable of extending the mature life phase of a nematode, comprising:
   contacting a nematode with a test agent, said organism having a cholinergic pathway and an insulin signaling pathway;
   assaying for the ability of the test agent to inhibit the cholinergic pathway and insulin signaling pathway by:
   (i) monitoring the effect of the test agent on one or more of the expression, intracellular level, extracellular level, activity, post-translational modification, interaction or cellular localization of at least one indicator of said cholinergic pathway, wherein the indicator of said cholinergic pathway is selected from the group consisting of EGL-8, RIC-8-and RIC-4; and
   (ii) monitoring the effect of the test agent on one or more of the expression, intracellular level, extracellular level, activity, post-translational modification, interaction, cellular localization of DAF-2;
   and selecting an agent that inhibits the cholinergic pathway and DAF-2;
   to thereby identify an agent capable of extending the mature life phase of a nematode.

4. The method of claim 2, wherein the agent is identified based on its ability to alter expression of said indicator.

5. The method of claim 2, wherein the agent is identified based on its ability to alter an intracellular level of said indicator.

6. The method of claim 2, wherein the agent is identified based on its ability to alter an activity of said indicator.

7. The method of claim 2, wherein the agent is identified based on its ability to alter the cellular localization of said indicator.

8. The method of any one of claims 1, 2 and 3, wherein the nematode is *C. elegans*.

9. The method of claim 8, wherein the nematode is a parasitic nematode.

10. A method for identifying an agent capable of extending the mature life phase of a nematode, comprising:
   contacting a cell from said nematode with a test agent, said cell having a cholinergic pathway;
   assaying for the ability of the test agent to inhibit the cholinergic pathway by monitoring the effect of the test agent on one or more of the expression, intracellular level, extracellular level, activity, post-translational modification, interaction or cellular localization of an indicator of said cholinergic pathway, wherein the indicator of said cholinergic pathway is selected from the group consisting of EGL-8, RIC-8 and RIC-4; and
   selecting an agent that inhibits the cholinergic pathway;
   to thereby identify an agent capable of extending the mature life phase of a nematode.

11. A method for identifying an agent capable of extending the mature life phase of a nematode, comprising:
   contacting a cell from said nematode with a test agent, said cell having a cholinergic pathway and an insulin signaling pathway;
   assaying for the ability of the test agent to inhibit the cholinergic pathway and insulin signaling pathway by:
   (i) monitoring the effect of the test agent on one or more of the expression, intracellular level, extracellular level, activity, post-translational modification, interaction or cellular localization of an indicator of said cholinergic pathway, wherein the indicator of said cholinergic pathway is selected from the group consisting EGL-8, RIC-8-and RIC-4;
   (ii) and monitoring the effect of the test agent on one or more of the expression, intracellular level, extracellular level, activity, post-translational modification, interaction, cellular localization, DAF-2; and
   selecting an agent that inhibits the cholinergic pathway and DAF-2; to thereby identify an agent capable of extending the mature life phase of a nematode.

12. A method for identifying an agent capable of extending the mature life phase of a nematode, comprising:
   contacting a cell population from said nematode with a test agent, said population comprising a cell having a cholinergic pathway and a cell having an insulin signaling pathway; assaying for the ability of the test agent to inhibit the cholinergic pathway and insulin signaling pathway by:
   (i) monitoring the effect of the test agent on one or more of the expression, intracellular level, extracellular level, activity, post-translational modification, interaction or cellular localization of an indicator of said cholinergic pathway, wherein the indicator of said cholinergic pathway is selected from the group consisting EGL-8, RIC-8 and RIC-4;
   (ii) and monitoring the effect of the test agent on one or more of the expression, intracellular level, extracellular level, activity, post-translational modification, interaction, cellular localization DAF-2; and
   selecting an agent that inhibits the cholinergic pathway and DAF-2;
   to thereby identify an agent capable of extending the mature life phase a nematode.

13. The method of any one of claims 10-12, wherein the agent is identified based on its ability to alter expression of said indicator of said cholinergic pathway.

14. The method of any one of claims 10-12, wherein the agent is identified based on its ability to alter an intracellular or extracellular level of said indicator of said cholinergic pathway.

15. The method of any one of claims 10-12, wherein the agent is identified based on its ability to alter an activity of said indicator of said cholinergic pathway.

16. The method of any one of claims 10-12, wherein the agent is identified based on its ability to alter the cellular localization of said indicator of said cholinergic pathway.

17. The method of claim 12, wherein the cell population comprises presynaptic cells and postsynaptic cells.

18. The method of claim 17, wherein the presynaptic cells are nerve cells.

19. The method of claim 17, wherein the postsynaptic cells are nerve cells.

20. The method of claim 17, wherein the postsynaptic cells are muscle cells.

21. A method for identifying an agent capable of extending the mature life phase of a nematode, comprising:
   contacting of a nematode with a test agent, said nematode having a cholinergic pathway and decreased activity or expression DAF-2;
   assaying for the ability of the test agent to inhibit the expression or activity of an indicator of said cholinergic pathway selected from the group consisting of EGL-8, RIC-8 and RIC-4;
   wherein the ability of said agent to inhibit the expression or activity of said indicator of said cholinergic pathway identifies said agent as capable of extending the mature life phase of a nematode.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
caatgagcaa tgtggacagc                                              20

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
ccgtctggtc gttgtctttt                                              20
```